(12) United States Patent
Andini et al.

(10) Patent No.: US 12,264,365 B2
(45) Date of Patent: Apr. 1, 2025

(54) POLYNUCLEOTIDES FOR AMPLIFICATION AND DETECTION OF SARS-CoV-2

(71) Applicant: Talis Biomedical Corporation, Chicago, IL (US)

(72) Inventors: Nadya Andini, Livermore, CA (US); Kathy Chiu, Irvine, CA (US); Xuewen Jiang, Menlo Park, CA (US); Hédia Maamar, San Jose, CA (US)

(73) Assignee: Talis Biomedical Corporation, Chicago, IL (US)

( * ) Notice: Subject to any disclaimer, the term of this patent is extended or adjusted under 35 U.S.C. 154(b) by 402 days.

(21) Appl. No.: 16/912,462

(22) Filed: Jun. 25, 2020

(65) Prior Publication Data

US 2021/0292854 A1   Sep. 23, 2021

Related U.S. Application Data

(60) Provisional application No. 63/009,803, filed on Apr. 14, 2020, provisional application No. 62/993,523, filed on Mar. 23, 2020.

(51) Int. Cl.
| | | |
|---|---|---|
| *C12Q 1/6876* | (2018.01) | |
| *C12Q 1/6813* | (2018.01) | |
| *C12Q 1/6844* | (2018.01) | |
| *C12Q 1/70* | (2006.01) | |

(52) U.S. Cl.
CPC ......... *C12Q 1/6876* (2013.01); *C12Q 1/6813* (2013.01); *C12Q 1/6844* (2013.01); *C12Q 1/70* (2013.01); *C12Q 2521/101* (2013.01); *C12Q 2521/107* (2013.01); *C12Q 2531/119* (2013.01); *C12Q 2600/112* (2013.01)

(58) Field of Classification Search
None
See application file for complete search history.

(56) References Cited

U.S. PATENT DOCUMENTS

| | | |
|---|---|---|
| 5,155,018 A | 10/1992 | Gillespie et al. |
| 5,173,401 A | 12/1992 | Wolff et al. |
| 5,234,809 A | 8/1993 | Boom et al. |
| 5,389,515 A | 2/1995 | Chmelo et al. |
| 5,512,445 A | 4/1996 | Yang et al. |
| 5,804,141 A | 9/1998 | Chianese |
| 5,830,643 A | 11/1998 | Yamamoto et al. |
| 6,001,611 A | 12/1999 | Will |
| 6,383,393 B1 | 5/2002 | Colpan et al. |
| 7,504,111 B2 | 3/2009 | Fontana et al. |
| 7,728,119 B2 | 6/2010 | Nakamura et al. |
| 7,897,744 B2 | 3/2011 | Plummer et al. |
| 8,993,718 B2 | 3/2015 | Gross et al. |
| 9,187,789 B2 | 11/2015 | Pabich et al. |
| 9,434,999 B1 | 9/2016 | Ao et al. |
| 9,982,312 B2 | 5/2018 | Pearce et al. |
| 9,994,916 B2 | 6/2018 | Thornton et al. |
| 10,252,264 B2 | 4/2019 | Shen et al. |
| 10,450,616 B1 | 10/2019 | Dedent et al. |
| 10,500,267 B2 | 12/2019 | LeFebvre et al. |
| 10,907,222 B2 | 2/2021 | Jeon et al. |
| 10,954,572 B2 | 3/2021 | Dedent et al. |
| 11,047,007 B1 | 6/2021 | Andini et al. |
| 11,326,214 B2 | 5/2022 | Dedent et al. |
| 2004/0091870 A1 | 5/2004 | Pabich et al. |
| 2004/0132218 A1 | 7/2004 | Ho |
| 2006/0216212 A1 | 9/2006 | Lum et al. |
| 2006/0257874 A1 | 11/2006 | Tisi et al. |
| 2007/0061898 A1 | 3/2007 | Yang et al. |
| 2007/0087336 A1 | 4/2007 | Sampath et al. |
| 2007/0161590 A1 | 7/2007 | Van Bilsen et al. |
| 2007/0202523 A1 | 8/2007 | Becker et al. |
| 2008/0152587 A1 | 6/2008 | Zhou et al. |
| 2008/0276335 A1 | 11/2008 | Abad et al. |
| 2008/0299567 A1 | 12/2008 | Marshall et al. |
| 2008/0318282 A1 | 12/2008 | Uematsu et al. |
| 2009/0130656 A1 | 5/2009 | Whiley et al. |
| 2009/0226885 A1 | 9/2009 | Sillekens et al. |
| 2009/0253622 A1 | 10/2009 | Van Noort et al. |
| 2010/0021886 A1 | 1/2010 | Wang et al. |
| 2010/0267012 A1 | 10/2010 | Bergeron et al. |
| 2012/0052503 A1 | 3/2012 | Li |
| 2012/0100551 A1 | 4/2012 | Kojima et al. |

(Continued)

FOREIGN PATENT DOCUMENTS

| | | |
|---|---|---|
| CN | 1592792 A | 3/2005 |
| CN | 101305101 A | 11/2008 |

(Continued)

OTHER PUBLICATIONS

Zhang et al., "Rapid Molecular Detection of SARS-CoV-2 (Covid-19) Virus RNA Using Colorimetric LAMP," MedRxiv, Feb. 29, pp. 1-14. (Year: 2020).*

Bakheit et al.; Sensitive and specific detection of cryptosporidium species in PCR-negative samples by loop-mediated isothermal DNA amplification and confirmation of generated LAMP products by sequencing; Veterinary Parasitology; 158(1-2); pp. 11-22; Nov. 2008.

Beaucage et al.; Deoxynucleoside phosphoramidites - a new class of key intermediates for deoxypolynucleotide synthesis; Tetrahedron Letters; 22(20); pp. 1859-1862; Jan. 1981.

(Continued)

*Primary Examiner* — Young J Kim
(74) *Attorney, Agent, or Firm* — Shay Glenn LLP

(57) ABSTRACT

Disclosed herein are primers and probes related to the detection of SARS-CoV-2 via nucleic acid amplification testing (NAAT), for example to amplify and determine the presence of SARS-CoV-2 in test samples and/or to diagnose Covid-19. Specifically, the present disclosure describes primers and probes that bind to the N gene, ORF1ab, or E gene of SARS-CoV-2 coronavirus for detection via loop mediated isothermal amplification (LAMP) and molecular beacon hybridization.

24 Claims, No Drawings
Specification includes a Sequence Listing.

(56) References Cited

U.S. PATENT DOCUMENTS

| | | |
|---|---|---|
| 2013/0017539 A1 | 1/2013 | Singhal et al. |
| 2013/0039938 A1 | 2/2013 | Smith et al. |
| 2013/0265054 A1 | 10/2013 | Lowery et al. |
| 2013/0323738 A1 | 12/2013 | Tanner et al. |
| 2014/0072971 A1 | 3/2014 | Wuitschick et al. |
| 2014/0308663 A1 | 10/2014 | Yonekawa et al. |
| 2014/0349295 A1 | 11/2014 | Hosaka et al. |
| 2015/0159205 A1 | 6/2015 | Narayanan et al. |
| 2015/0267266 A1 | 9/2015 | Soetaert et al. |
| 2015/0322493 A1 | 11/2015 | Tulp et al. |
| 2016/0024562 A1 | 1/2016 | Pabich et al. |
| 2016/0076083 A1 | 3/2016 | Ellington et al. |
| 2016/0257998 A1 | 9/2016 | Persing et al. |
| 2016/0273029 A1 | 9/2016 | Suwara et al. |
| 2016/0289730 A1 | 10/2016 | Pezacki et al. |
| 2016/0319378 A1 | 11/2016 | Rey |
| 2017/0260572 A1 | 9/2017 | Filer et al. |
| 2017/0283884 A1 | 10/2017 | Knudsen |
| 2019/0111423 A1 | 4/2019 | Ismagilov et al. |
| 2019/0284617 A1 | 9/2019 | Lee et al. |
| 2019/0284618 A1 | 9/2019 | Dedent et al. |
| 2021/0164043 A1 | 6/2021 | Casolan et al. |
| 2021/0254139 A1 | 8/2021 | Dedent et al. |
| 2021/0340622 A1 | 11/2021 | Andini et al. |
| 2022/0251630 A1 | 8/2022 | Dedent et al. |

FOREIGN PATENT DOCUMENTS

| | | |
|---|---|---|
| CN | 101831488 A | 9/2010 |
| CN | 101886122 A | 11/2010 |
| CN | 102559861 A | 7/2012 |
| CN | 102918155 A | 2/2013 |
| CN | 107099618 A | 8/2017 |
| JP | 2012060940 A | 3/2012 |
| JP | 2012130290 A | 7/2012 |
| JP | 5710190 B2 | 4/2015 |
| JP | 2017038572 A | 2/2017 |
| KR | 101742016 B1 | 5/2017 |
| WO | WO2002/079243 A2 | 10/2002 |
| WO | WO2006/133385 A2 | 12/2006 |
| WO | WO2007/096184 A1 | 8/2007 |
| WO | WO2009/099037 A1 | 8/2009 |
| WO | WO2010/010951 A1 | 1/2010 |
| WO | WO2011/004397 A1 | 1/2011 |
| WO | WO2011/091330 A1 | 7/2011 |
| WO | WO2011/144304 A1 | 11/2011 |
| WO | WO2012/021802 A2 | 2/2012 |
| WO | WO2012/032489 A1 | 3/2012 |
| WO | WO2013/132452 A2 | 9/2013 |
| WO | WO2015/058008 A2 | 4/2015 |
| WO | WO2015/147415 A1 | 10/2015 |
| WO | WO2016/011280 A1 | 1/2016 |
| WO | WO2016/085632 A2 | 6/2016 |
| WO | WO2017/103269 A1 | 6/2017 |
| WO | WO2017/192902 A1 | 11/2017 |
| WO | WO2018/031531 A1 | 2/2018 |
| WO | WO2019/133727 A1 | 7/2019 |
| WO | WO2020/142754 A2 | 7/2020 |
| WO | WO2021/016602 A1 | 1/2021 |
| WO | WO2021/113267 A1 | 6/2021 |
| WO | WO2021/195103 A1 | 9/2021 |

OTHER PUBLICATIONS

Broude; Stem-loop oligonucleotides: a robust tool for molecular biology and biotechnology; Trends in Biotechnology; 20(6); pp. 249-256; Jun. 2002.

Cady; Quantum dot molecular beacons for DNA detection; Micro and Nano Technologies in Bioanalysis; 554; pp. 367-379; 2009 (the year of publication is sufficiently earlier than the effective U.S. filing date and any foreign priority date so that the particular month of publication is not in issue).

Choopara et al.; Development of chlamydia trachomatis detection by loop-mediated isothermal amplification; International Journal of Biomedical Sciences and Bioformatics; 2(1); pp. 21-25; 2015 (the year of publication is sufficiently earlier than the effective U.S. filing date and any foreign priority date so that the particular month of publication is not in issue).

Choopara et al.; Rapid and visual chlamydia trachomatis detection using loop-mediated isothermal amplification and hydroxynaphthol blue; Letters in Applied Microbiology; 64(1); pp. 51-56; Sep. 2016.

Cissell et al.; Resonance energy transfer methods of RNA detection; Analytical and Bioanalytical Chenistry; 393(1); pp. 125-135; Jan. 2009.

Edwards et al.; Loop-mediated isothermal amplification test for detection of neisseria gonorrhoeae in urine samples and tolerance of the assay to the presence of urea; Journal of Clinical Microbiology; 52(6); pp. 2163-2165; Jun. 2014.

Eiken Chemical Co.; A guide to LAMP primer designing, Primer-Explorer V4; 19 pages; retrieved from the internet(https://primerexplorer.jp/e/v4_manual/pdf/PrimerExplorerV4_Manual_1.pdf) on Oct. 20, 2022.

Fan et al.; The Development and evaluation of a loop-mediated isothermal amplification method for the rapid detection of salmonella enterica serovar typhi; Plos One; 10(4); eo124507; 13 pages; Apr. 2015.

Gandelman et al.; Loop-mediated amplification accelerated by stem primers; International Journal of Molecular Sciences; pp. 9108-9124; Dec. 2011.

GenBank Accession No. X67293, N. gonorrhoeae gene for 23S rRNA, 2pages; retrieved from the internet (https:ncbi.nlm.nih.gov/nucleotide/X67293.1?report=genobank&log$=nuclalign&blast_rank=95&RID=XZXX9U6R016) on Jan. 13, 2022.

Genbank submission AC127341.3; Mus musculus BAC clone RP23-189L19 from chromosome 17, complete sequence; Nov. 23, 2003 [Online]; 2 pages; retrieved from the internet (https://www.ncbi.nlm.nih/nuccore/AC127341) on Jul. 29, 2021.

Genbank submission AE004969.1, Neisseria gonorrhoeae FA 1090 complete genome, 2 pages; Jul. 1, 2015 [online]; retrieved from the internet (https://www.ncbi.nlm.nih.gov/nuccore/AE004969) on Nov. 23, 2020.

Genbank submission AFY24545.1; glycoprotien 5 (Porcine reproductive and respiratory syndrome virus; Feb. 28, 2013 [online]; 2 pages; retrieved from the internet (https://www.nobi.nim.gov/prtein/AFY24545) on Jul. 29, 2021.

Genbank submission AL16244.1; Tetraodon nigroviridis genome survey sequence PC-Ori end clone 198J04 of library G from Tetraodon nigroviridis, genomic survey sequence, Sep. 1, 2000 [online] 2 pages; retrieved from the internet (https://www.ncbi.nlm.nih.gov/nuccore/AL169244) on Jul. 29, 2021.

Genbank submission CP019169.1; Betaproteobacteria bacterium GR16-43 chromosome, complete genome; Jan. 17, 2017 [online]; 2 pages; retrieved from the internet (https://www.nobi.nim.nih.gov/nuccore/CP019169) on Jul. 29, 2021.

Genbank submission CZ791141.1, OC_Ba0158F23.fOC_BaOryza coarctata genomic clone OC_Ba158F23 5', genomic survey sequence; Aug. 29, 2012 [online]; 2 pages; retrieved from the internet (https://www.ncbi.nlm.nih.gov/nuccore/CZ791141.1) on Jul. 29, 2021.

Genbank submission EK565433.1, 1095521038908 Global-Ocean-Sampling_GS-32-01-01-1P3-1P6KB marine metagenome genomic clone 1061005966854 5' genomic survey sequence, 2 pages; May 26, 2010 [online]; retrieved from the internet (https://www.ncbi.nlm.nih.gov/nuccore/EK565433 on Nov. 23, 2020.

Genbank submission HS475166.1, BL-57332 Nilaparvata lugens illumina library Nilaparvatalugens cDNA 5', mRNA sequence, May 3, 2011 [online]; 1 page; retrieved from the internet (https://www.nobi.nim.nih.gov/nuccore/HS475166) on Jul. 29, 2021.

Genbank submission LR606187.1; Aquila chrysaetos chrysaetos genome assembly, chromosome; Jul. 4, 2019 [online] 1 page; retrieved from the internet (https:/www.ncbi.nlm.nih.gov/nuccore/LR606187) on Nov. 23, 2020.

Genbank submission LS483369.1, Neisseria cinerea strain NCTC10294 genome assembly, chromosome: 1, Jun. 17, 2018 [online]; 1 page; retrieved from the internet (https://www.nobi.nim.nih.gov/nuccore/LS483369) on Nov. 23, 2020.

(56) References Cited

OTHER PUBLICATIONS

Iwamoto et al.; Loop-mediated isothermal amplification for direct detection of mycobacterium tuberculosis complex m. avium, and m. intracellulare in sputum samples; Journal of clinical Microbiology; 41(6); pp. 2616-2622; Jun. 2003.
Jepsen et al.; Locked nucleic acid: potent nucleic acid analog in therapeutics and biotechnology; Oligonucleotides; 14(2); pp. 130-146; 2004 (the year of publication is sufficiently earlier than the effective U.S. filing date and any foreign priority date so that the particular month of publication is not in issue).
Jevtusevskaja et al.; Combination with antimicrobial peptide lyses improves loop-mediated isothermal amplification based method for chlamydia trachomatis detection directly in urine sample; BMC Infectious Diseases; 16(329): pp. 1-8; Jul. 2016.
Johns Hopkins University; Coronavirus resource center; 1 page; retrieved from the internet (https://coronavirus.jhu.edu/map.html) on Oct. 14, 2022.
Juskowiak; Nucleic acid-based fluorescent probes and their analytical potential; Analytical and Bioanalytical Chemistry; 399(9); pp. 3157-3176; Mar. 2011.
Katoh et al.; MAFFT multiple sequence alignment software version 7: improvements in performance and useability; Molecular Biology and Evolution; 30(4); pp. 772-780; Apr. 2013.
Lee et al.; Clinical evaluation of a loop-mediated isothermal amplification (LAMP) assay for rapid detection of neisseria meningitidis in cerebrospinal fluid; Plos One; 10(4); e0122922; 13 pages; Apr. 2015.
Li et al.; Molecular beacons: an optimal multifunctional biological probe; Biochemical and Biophysical Research Communications; 373(4); pp. 457-461; Sep. 2008.
Little et al.; Strand displacement amplification and homogeneous real-time detection incorporated in a second-generation dna probe system, BDProbe TecET; Clinical Chemistry; 45(6); pp. 777-784; Jun. 1999.
Liu et al.; Establishment of an accurate and fast detection method using molecular beacons in loop-mediated isothermal amplification assay; Scientific reports; 7(1); pp. 1-9; doi:10.1038/srep40125; Jan. 2017.
Liu et al.; Loop-mediated isothermal amplification of neisseria gonorrhoeae porA pseudogene: a rapid and reliable method to detect gonorrhea; AMB Express; 6; p. 48; doi 10.1186/s13568-017-0349-6; 7 pages; Dec. 2017.
Lowe et al.; A computer program for selection of olignucleotide primers for polymerase chain reactions; Nucleic Acids Research; 18(7); pp. 1757-1761; Apr. 1990.
Nagamine et al.; Accelerated reaction by loop-mediated isothermal amplification using loop primers; 16(3); pp. 223-229; Jun. 2002.
Needham-Vandevanter et al.; Characterization of an adduct between CC-1065 and a defined oligodeoxynucleotide duplex; Nucleic Acids Research.; 12(15); pp. 6159-6168; Aug. 1984.
Neejara et al.; Rapid detection and differentiation of dengue virus serotypes by NSI specific reverse transcription loop-mediated isothermal amplification (RT-LAMP) assay in patients presenting to a tertiary care hospital in Hyderabad India; Journal of Virological Methods; 211; pp. 22-31; Jan. 2015.
Ng et al.; The laboratory diagnosis of neisseria gonorrhoeae; Canadian Journal of Infectious Diseases and Medical Microbiology; 16(1); pp. 15-25; Oct. 2005.
Nixon et al.; A novel approach for evaluating the performance of real time quantitative loop-mediated isothermal amplification-based methods; Biomolecular Detection and Quantification; vol. 2; pp. 4-10; Dec. 2014.
NJIRU; Loop-mediated isothermal amplification technology: towards point of care diagnostics; Plos Neglected Tropical Diseases; 6(6); e1572; 4 pages; Jun. 2012.
Sievers et al.; Fast, scaleable generation of high-quality protein multiple sequence alignments using clustal omega; Molecular Systems Biology; 7(1); 539; doi: 10.1038/msb.2011.75; 6 pages; 2011 (the year of publication is sufficiently earlier than the effective U.S. filing date and any foreign priority date so that the particular month of publication is not in issue).
Tanner et al.; Simultaneous multiple target detection in real-time loop-mediated isothermal amplification; Biotechniques; 53(2); pp. 81-89; Aug. 2012.
Trembizki; Direct real-time PCR- based detection of neisseria gonorrhoeae 23S rRNA mutations associated with azithromycin resistance; Journal of Antimicrobial Chemotherapy: 70(12); pp. 3244-3249; Dec. 2015.
Tyagi et al.; Multicolor molecular beacons for allele discrimination; Nature Biotechnology; 16(1); pp. 49-53; Jan. 1998.
Wang et al.; Molecular engineering of DNA: molecular beacons: Angewandle Chemie International Edition; 48(5); pp. 856-870; 34 pages; (Author Manuscript) Jan. 2009.
Wang et al.; Rapid and sensitive detection of shigella spp. And *Salmonella* spp. By multiple endonuclease restriction real-time loop-mediated isothermal amplification technique; The Journal of Molecular Diagnostics; 17(4); pp. 392-401; Jul. 2015.
Wang et al.; Two methods for increased specificity and sensitivity in loop-mediated isothermal amplification; Molecules; 20(4); pp. 6048-6059; Apr. 2015.
Wong et al.; Loop-mediated isothermal amplification (LAMP) a versatile technique for detection of micro-organisms; Journal of Applied Microbiology; 124(3); pp. 626-643; Mar. 2018.
World Health Organization; The use of commercial loop-mediated isothermal amplification assay (TB-LAMP) for detection of tuberculosis; Expert Group meeting Report Geneva; vol. 2013; pp. 1-50; May 2013.
Xu et al.; A capillary-based multiplexed isothermal nucleic acid-based test for sexually transmitted diseases in patients; Chemical Communications; 52(82); pp. 12187-12190; Sep. 2016.
Xu et al.; Rapid ultrasonic isothermal amplification of DNA with multiplexed melting analysis—applications in the clinical diagnosis of sexually transmitted diseases; Chemical Communications; 51(13); pp. 2589-2592; Jan. 2015.
Yamamoto et al.; Molecular beacon aptamer fluoresces in the presence of Tat protein of HIV-1; Genes to Cells; 5(5); pp. 389-396; May 2000.
Yamamura et al.; Evaluation of a new rapid molecular diagnostic system for plasmodium falciparum combined with DNA filter paper, loop-mediated isothermal amplification, and melting curve analysis; Jpn J. Infect. Dis.; 62 (1); pp. 20-25; Jan. 2009.
Zanoli et al.; Isothermal amplification methods for the detection of nucleic acids in microfluidic devices; Biosensors; 3(1); pp. 18-43; Dec. 2012.
Zhnag et al.; Rapid molecular detection of SARS-COV-2 (COVID-19) virus RNA using colorimetric; MedRxiv; pp. 1-14; doi.org/10.1101/2020.02.26.20028373; Jan. 2020.
Dedent et al.; U.S. Appl. No. 17/718,025 entitled Polynucleotides for the amplification and detection of chlamydia trachomatis; filed Apr. 11, 2022.
Casolari et al.; U.S. Appl. No. 17/778,486 entitled "Polynucleotides for the amplfication and detection of human beta actin," filed May 20, 2022.
Chui et al.; A comparison of three real-time PCR assays for the confirmation of Neisseria gonorrhoeae following detection of N. gonorrhoeae using Roche COBAS AMPPLICOR. Clinical microbiology and infection; 14(5); pp. 473-479; May 1, 2008.
Falk et al.; Sampling for Chlamydia trachomatis infection comparison of vaginal, first-catch urine, combined vaginal and first-catch urine and endocervical sampling; International journal of STD & AIDS; 21(4); pp. 283-287; Apr. 2010.
GenBank Accession No. NC045512; Severe acute respiratory syndrome coronavirus 2 isolate Wuhan-Hu-1, complete genome; 2 pages; retrieved from the internet (https://www.ncbi.nim.nih.gov/nuccore/NC_045512.2?report=genbank&from=26523&to=27191) on Apr. 7, 2023.
Kubota et al.; FRET-based assimilating probe for sequence-specific real-time monitoring of loop-mediated isothermal amplification (LAMP); Biological Engineering Transactions; 4(2); pp. 81-100; Jan. 2011.

(56) References Cited

OTHER PUBLICATIONS

Lu et al.; Genus-wide comparative genomics analysis of Neisseria to identify new genes associated with pathogenicity and niche adaptation of Neisseria pathogens; International journal of genomics; vol. 2019; 19 pages; Jan. 15, 2019.
Marras et al.; Efficiencies of fluorescence resonance energy transfer and contact?mediated quenching in oligonucleotide probes; Nucleic acids research; 30(21); e122; 8 pages; Nov. 1, 2002.
Meyer et al.; The laboratory diagnosis of Neisseria gonorrhoeae: current testing and future demands. Pathogens; 9(2): 91; pp. 1-19; Jan. 31, 2020.
McClure et al.; Global network analysis of Neisseria gonorrhoeae identifies coordination between pathways, processes, and regulators expressed during human infection; Msystems ;5(1); pp. 10-128; Feb. 25, 2020.
Michel et al.; Chlamydia trachomatis load at matched anatomic sites: implications for screening strategies; Journal of clinical microbiology; 45(5); pp. 1395-1402; May 2007.
Notomi et al.; Loop-mediated isothermal amplification of DNA; Nucleic acids research; 28(12); e63; Jun. 15, 2000.
Papp et al.; Recommendations for the laboratory-based detection of Chlamydia trachomatis and Neisseria gonorrhoeae—2014; MMWR; Recommendations and reports: Morbidity and mortality weekly report. Recommendations and reports/Centers for Disease Control; 63(1); 19 pages; Mar. 3, 2014.
Priest et al.; Neisseria gonorrhoeae DNA bacterial load in men with symptomatic and asymptomatic gonococcal urethritis; Sexually Transmitted Infections ;93(7); pp. 478-481; Nov. 1, 2017.
Van Der Veer; Men and women have similar Neisseria gonorrhoeae bacterial loads: a comparison of three anatomical sites. Journal of Clinical Microbiology; 58(11); pp. 10-128; Oct. 21, 2020.
Zhang et al.; Enhancing colorimetric loop-mediated isothermal amplification speed and sensitivity with guanidine chloride; Biotechniques; 69(3); pp. 178-185; Jun. 2020.
Dedent et al.; U.S. Appl. No. 18/296,978 entitled "Polynucleotides for the amplification and detection of neisseria gonorrhoeae," filed Apr. 6, 2023.
Schachter et al.; Vaginal swabs are the specimens of choice when screening for Chlamydia trachomatis and Neisseria gonorrhoeae: results from a multicenter evaluation of the APTIMA assays for both infections; Sexually transmitted diseases; 32(12); pp. 725-728; Dec. 1, 2005.
Van Liere et al.; Spontaneous clearance of urogenital, anorectal and oropharyngeal Chlamydia trachomatis and Neisseria gonorrhoeae in women, MSM and heterosexual men visiting the STI clinic: a prospective cohort study. Sexually transmitted infections; 95(7); pp. 505-510; Nov. 1, 2019.
Zhang et al., Application of LAMP Technique in Detection of Pathogenic Microorganisms; South China Journal of Preventive Medicine; 33(5): 45-49; Oct. 2007 (with English Abstract).
Chaudhry et al.; Detection of Neisseria Gonorrhoeae by polymerase chain reaction (PCR); Indian Journal of Clinical Biochemistry; 14 (2); pp. 135-142; Jul. 1999.
Yu et al.; Rapid colorimetric detection of COVID-19 coronavirus using a reverse transcriptional loop-mediated isothermal amplification (RT-LAMP) diagnostic platform: iLACO; Medrxiv; XP055730128; DOI: 10.1101/2020.02.20.20025874; 19 pages; Feb. 24, 2020.
Genebank Accession No. CT573023; Mouse DNA Sequence from cline RP23-361611 on chromosone 13, complete sequence; 2 pages; retrieved from the internet (https://www.ncbi.nlm.nih.gov/nuccore/CT573023) on Nov. 2, 2022.
Genebank Accession No. LR744041s10; Scyliorhinus canicula genome assembly, chromosome: 12; 1 page; retrieved from the internet (http://www.ncbi.nlm.nih.gov/nucore/LR744041) on Oct. 30, 2022.
Genebank Accession No. LR812501.1; Danilo aesculapii genome assembly, chromosone: 21; 5 pages; retrieved from the internet (http://www.ncbi.nlm.nih.gov/nuccore/LR812501) on Oct. 30, 2022.
Kimura et al.; Point of care testing chip for multiple virus infection detection using LAMP; 2019 IEEE 32nd International Conference on Micro Electro Mechanical Systems (MEMS); pp. 83-86; Jan. 27, 2019.
Brown et al.; U.S. Appl. No. 18/444,250 entitled "Polynucleotides for the amplification and detection of influenza a," filed Feb. 16, 2024.
Brown et al.; U.S. Appl. No. 18/444,298 entitled "Polynucleotides for the amplification and detection of influenza b," filed Feb. 16, 2024.

\* cited by examiner

POLYNUCLEOTIDES FOR AMPLIFICATION AND DETECTION OF SARS-CoV-2

CROSS-REFERENCE TO RELATED APPLICATIONS

This application claims the benefit of U.S. Provisional Application No. 62/993,523, filed Mar. 23, 2020, and U.S. Provisional Application No. 63/009,803, filed Apr. 14, 2020, the contents of which are each incorporated by reference in their entirety.

SEQUENCE LISTING

The instant application contains a Sequence Listing which has been submitted electronically in ASCII format and is hereby incorporated by reference in its entirety. Said ASCII copy, created on Jul. 6, 2020, is named TSM-055US2_SL.txt and is 23,595 bytes in size.

FIELD OF THE INVENTION

The present invention relates to the fields of molecular biology and nucleic acid chemistry. The invention provides methods and reagents for detecting the SARS-CoV-2 virus, the causative agent for the disease referred to as COVID-19. The invention also relates to the fields of medical diagnostics and prognostics. In particular, the invention relates to polynucleotides and methods for amplifying and detecting certain genes in the SARS-CoV-2 viral genome.

BACKGROUND

There is an urgent need for the development of a rapid, affordable, sample-in answer-out point of care (POC) diagnostic platform for the novel coronavirus spreading across the globe. On 11 Mar. 2020, the World Health Organization (WHO) declared COVID-19, which is caused by the SARS-CoV-2 virus, to be a pandemic based on 118,000 cases in 114 countries and 4,291 deaths. Ten days later, the Johns Hopkins Coronavirus Resource Center (https://coronavirus.jhu.edu/map.html) reported 329,858 confirmed cases with 14,380 deaths worldwide. Three months later, there are over 8.5 million confirmed cases worldwide and the death toll is nearly half a million people with little indication that spread of the disease is slowing. Throughout this public health crisis, the inability to test members of the public for infection with SARS-CoV-2 has significantly hampered efforts to contain the pandemic.

The compositions and methods disclosed herein provide primers and probes for the detection of the SARS-CoV-2 RNA virus using loop-mediated isothermal amplification.

SUMMARY OF THE INVENTION

The present invention encompasses, in some embodiments, a composition comprising a set of polynucleotides selected from the group consisting of Set-1 through Set-17. In some embodiments, the composition further comprises a probe. In some embodiments, the probe comprises a label. In some embodiments, the probe is a labeled polynucleotide. In a preferred implementation, the label is a fluorophore, which preferably is covalently attached to a terminus of the polynucleotide. In a particularly preferred embodiment, the probe or polynucleotide is a molecular beacon comprising a fluorophore, a quencher, and a polynucleotide. In one embodiment, the fluorophore is FAM and the quencher is Black Hole Quencher 1 (BHQ1; LGC Biosearch Technologies). In an alternate implementation, the fluorophore is ATTO 565 or Alexa 594 or Cy5 and the quencher is BHQ1 or BHQ2.

In some implementations, composition comprises a labeled polynucleotide comprising a sequence selected from the group consisting of nucleotides 5-27 of SEQ ID NO.: 55, nucleotides 7-25 of SEQ ID NO.: 56, nucleotides 5-22 of SEQ ID NO.: 75, nucleotides 5-22 of SEQ ID NO.: 76, nucleotides 5-29 of SEQ ID NO.: 77, nucleotides 6-26 of SEQ ID NO.: 78, nucleotides 5-29 of SEQ ID NO.: 79, nucleotides 5-22 of SEQ ID NO.: 80, nucleotides 5-22 of SEQ ID NO.: 81, nucleotides 4-22 of SEQ ID NO.: 82, nucleotides 6-28 of SEQ ID NO.: 83, nucleotides 6-25 of SEQ ID NO.: 84, nucleotides 3-23 of SEQ ID NO.: 85, and nucleotides 2-24 of SEQ ID NO.: 95. In further implementations, the labeled polynucleotide can comprise a sequence elected from the group consisting of SEQ ID NO.: 55, SEQ ID NO.: 56, SEQ ID NOS.: 75 through 85, and SEQ ID NO.: 95. In certain implementations, the sequence of the labeled polynucleotide is selected from the group consisting of SEQ ID NO.: 55, SEQ ID NO.: 56, SEQ ID NOS.: 75 through 85, and SEQ ID NO.: 95.

In certain implementations, the composition targets the first open reading frame of SARS-CoV2 (ORF1ab). In such implementation, the set of polynucleotides can be Set-11 or Set-13, and the labeled polynucleotide comprises a sequence selected from the group consisting of nucleotides 5-29 of SEQ ID NO.: 77 and nucleotides 5-29 of SEQ ID NO.: 79. In some embodiments, the labeled polynucleotide comprises SEQ ID NO.: 79, or more preferably SEQ ID NO.: 77. Preferably, the set of polynucleotides is Set-11. In another implementation targeting ORF1ab, the set of polynucleotides is Set-12 and the labeled polynucleotide comprises nucleotides 6-26 of SEQ ID NO.: 78. In some implementations, the labeled polynucleotide comprises SEQ ID NO.: 78.

In certain implementations, the composition targets gene N, which encodes a nucleoprotein that packages the positive strand viral genome RNA into a helical ribonucleocapsid (RNP) and plays a fundamental role during virion assembly through its interactions with the viral genome and membrane protein M. In such implementations, the set of polynucleotides can be Set-5 or Set-9 and the labeled polynucleotide comprises a sequence selected from the group consisting of nucleotides 5-22 of SEQ ID NO.: 75, nucleotides 5-22 of SEQ ID NO.: 76, nucleotides 5-22 of SEQ ID NO.: 80, nucleotides 5-22 of SEQ ID NO.: 81, nucleotides 4-22 of SEQ ID NO.: 82, nucleotides 6-28 of SEQ ID NO.: 83, nucleotides 6-25 of SEQ ID NO.: 84, nucleotides 3-23 of SEQ ID NO.: 85. In some embodiments, the labeled polynucleotide comprises a sequence selected from the group consisting of SEQ ID NO.: 75, SEQ ID NO.: 76, SEQ ID NO.: 80, SEQ ID NO.: 81, SEQ ID NO.: 82, SEQ ID NO.:83, SEQ ID NO.: 84, and SEQ ID NO.: 85. Preferably, the set of polynucleotides is Set-9. Similarly, the sequence of the labeled polynucleotides preferably is SEQ ID NO.: 83. In a second embodiment targeting the N gene, the set of polynucleotides is Set-1 or Set-4 and the labeled polynucleotide comprises nucleotides 5-27 of SEQ ID NO.: 55. In such embodiments, the labeled polynucleotide preferably comprises SEQ ID NO.: 55. In yet another embodiment targeting the N gene, the set of polynucleotides is Set-3 or Set-8 and the labeled polynucleotide comprises nucleotides 7-25 of SEQ ID NO.: 56. More preferably, the labeled polynucleotide comprises SEQ ID NO.: 56.

In certain implementations, the composition targets gene E, which encodes an envelope protein. In such implementations, the set of polynucleotides is selected from the group consisting of Set-14, Set-15, Set-16, and Set-17, and the labeled polynucleotide comprises nucleotides 2-24 of SEQ ID NO.: 95. More preferably, the labeled polynucleotide comprises SEQ ID NO.: 95. In a preferred implementation, the polynucleotide sequence of the molecular beacon consists of SEQ ID NO.:95.

In certain implementations, the composition for detecting the presence of SARS-CoV-2 comprises SEQ ID NO.: 49, SEQ ID NO.: 50, SEQ ID NO.: 51, SEQ ID NO.: 52, SEQ ID NO.: 53, and SEQ ID NO.: 54. In such an implementation, the composition can further comprise a molecular beacon comprising a fluorophore, a quencher, and SEQ ID NO. 83. In another implementation, the composition further comprises SEQ ID NO.: 63, SEQ ID NO.: 64, SEQ ID NO.: 65, SEQ ID NO.: 66, SEQ ID NO.: 67, and SEQ ID NO.: 68.

In yet another embodiment, the composition for detecting the presence of SARS-COV-2 comprises SEQ ID NO.: 63, SEQ ID NO.: 64, SEQ ID NO.: 65, SEQ ID NO.: 66, SEQ ID NO.: 67, and SEQ ID NO.: 68. This composition can further comprise a molecular beacon comprising a fluorophore, a quencher and SEQ ID NO. 77.

Yet another aspect of the invention provides a composition comprising a first set of polynucleotides comprising SEQ ID NO.: 49, SEQ ID NO.: 50, SEQ ID NO.: 51, SEQ ID NO.: 52, SEQ ID NO.: 53 and SEQ ID NO.: 66; and a second set of polynucleotides comprising SEQ ID NO.: 63, SEQ ID NO.: 64, SEQ ID NO.: 65, SEQ ID NO.: 66, SEQ ID NO.: 67 and SEQ ID NO.: 68. In some implementations, the composition further comprises a first labeled polynucleotide comprising nucleotides 6-28 of SEQ ID NO.: 83 and a second labeled polynucleotide comprising nucleotides 5-29 of SEQ ID NO.: 77. In some implementations, the first polynucleotide comprises SEQ ID NO.: 83 and the second labeled polynucleotide comprising SEQ ID NO.: 77.

In many implementations described herein, the probe is a molecular beacon comprising a fluorophore, a quencher, and a polynucleotide. In implementations wherein the set of polynucleotides is Set-5 or Set-9, the molecular beacon comprises a sequence selected from the group consisting of nucleotides 5-22 of SEQ ID NO.: 75, nucleotides 5-22 of SEQ ID NO.: 76, nucleotides 5-22 of SEQ ID NO.: 80, nucleotides 5-22 of SEQ ID NO.: 81, nucleotides 4-22 of SEQ ID NO.: 82, nucleotides 6-28 of SEQ ID NO.: 83, nucleotides 6-25 of SEQ ID NO.: 84, and nucleotides 3-23 of SEQ ID NO.: 85. More preferably, the molecular beacon comprises a sequence selected from the group consisting of SEQ ID NO.: 75, SEQ ID NO: 76, SEQ ID NO.: 80, SEQ ID NO.: 81, SEQ ID NO.: 82, SEQ ID NO.: 83, SEQ ID NO.: 84 and SEQ ID NO.: 85. Even more preferably, the polynucleotide sequence of the molecular beacon consists of a sequence selected from the group consisting of SEQ ID NO.: 75, SEQ ID NO: 76, SEQ ID NO.: 80, SEQ ID NO.: 81, SEQ ID NO.: 82, SEQ ID NO.: 83, SEQ ID NO.: 84 and SEQ ID NO.: 85. In other implementations, wherein the set of polynucleotides is Set-1 or Set-4, the molecular beacon comprises nucleotides 5-27 of SEQ ID NO.: 55, and more preferably comprises SEQ ID NO.: 55. In a preferred implementation, the polynucleotide sequence of the molecular beacon consists of SEQ ID NO.: 55. In implementations wherein the set of polynucleotides is Set-3 or Set-8, the molecular beacon comprises nucleotides 7-25 of SEQ ID NO.: 56, more preferably the full sequence SEQ ID NO.: 56. In a preferred implementation, the polynucleotide sequence of the molecular beacon consists of SEQ ID NO.: 56. In implementations, wherein the set of polynucleotides is Set-11 or Set-13, the molecular beacon comprises a sequence selected from the group consisting of nucleotides 5-29 of SEQ ID NO.: 77 and nucleotides 5-29 of SEQ ID NO.: 79. Preferably, the molecular beacon comprises a sequence selected from the group consisting of SEQ ID NO.: 77 and SEQ ID NO.: 79. In a particularly preferred implementation, the polynucleotide sequence of the molecular beacon consists of SEQ ID NO.: 77 or SEQ ID NO.: 79. In implementations wherein the set of polynucleotides is Set-12, the molecular beacon comprises nucleotides 6-26 of SEQ ID NO.: 78, more preferably the full sequence of SEQ ID NO.: 78. In a preferred implementation, the polynucleotide sequence of the molecular beacon consists of SEQ ID NO.: 78. In implementations, wherein the set of polynucleotides is Set-14, Set-15, Set16 or Set-17, the molecular beacon comprises nucleotides 2-24 of SEQ ID NO.: 95, more preferably the full sequence of SEQ ID NO.: 95. In a preferred implementation, The polynucleotide sequence of the molecule beacon consists of SEQ ID NO.: 95.

One aspect of the invention provides molecular beacons comprising a fluorophore, a quencher, and a polynucleotide, wherein the polynucleotide comprises a sequence selected from the group consisting of nucleotides 5-27 of SEQ ID NO.: 55, nucleotides 7-25 of SEQ ID NO.: 56, nucleotides 5-22 of SEQ ID NO.: 75, nucleotides 5-22 of SEQ ID NO.: 76, nucleotides 5-29 of SEQ ID NO.: 77, nucleotides 6-26 of SEQ ID NO.: 78, nucleotides 5-29 of SEQ ID NO.: 79, nucleotides 5-22 of SEQ ID NO.: 80, nucleotides 5-22 of SEQ ID NO.: 81, nucleotides 4-22 of SEQ ID NO.: 82, nucleotides 6-28 of SEQ ID NO.: 83, nucleotides 6-25 of SEQ ID NO.: 84, nucleotides 3-23 of SEQ ID NO.: 85, and nucleotides 2-24 of SEQ ID NO.: 95. In a preferred implementation, the polynucleotide portion of the molecular beacon comprises a sequence selected from the group consisting of SEQ ID NO.: 55, SEQ ID NO.: 56, SEQ ID NOS.: 75 through 85, and SEQ ID NO.: 95. More preferably, the sequence selected from the group consisting of SEQ ID NO.: 55, SEQ ID NO.: 56, SEQ ID NOS.: 75 through 85, and SEQ ID NO.: 95.

Yet another aspect of the invention provides method of detecting SARS-CoV-2 in a test sample, the method comprising (a) extracting nucleic acid from the test sample, (b) amplifying a target sequence by reacting the nucleic acid extracted in step (a) with a reaction mixture comprising a strand displacement DNA polymerase and a reverse transcriptase and a sequence specific primer set, wherein said sequence-specific primer set is selected from the group consisting of Set-1 through Set-17, and (c) detecting the presence or absence of an amplified product of step (b); wherein the presence of said amplification product is indicative of the presence of SARS-CoV-2 in the test sample. In one embodiment, the amplification in step (b) of the target sequence is performed between about 60° C. and about 67° C. for less than 30 minutes. Preferably, the amplification step is performed for less than fifteen minutes. In some implementations, the strand displacement DNA polymerase and the reverse transcriptase activities are provided by a single enzyme.

In certain embodiments, detecting the presence or absence of the amplification product comprises hybridizing the amplified product with a probe comprising a polynucleotide attached to a label. In a preferred implementation, the label is a fluorophore, which is preferably attached to a terminus of the polynucleotide. In a particularly preferred embodiment, the probe or polynucleotide is a molecular beacon comprising a fluorophore, a quencher, and a polynucleotide.

In one embodiment, the fluorophore is FAM and the quencher is BHQ1. In an alternate implementation, the fluorophore is ATTO 565 or Alexa 594 or Cy5 and the quencher is BHQ1 or BHQ2. In other implementations, detecting the presence or absence of the amplification product comprises exposing the amplified product to an intercalating dye.

Another aspect of the invention provides methods of detecting SARS-CoV-2 in a test sample, the method comprising (a) extracting nucleic acid from the test sample, (b) amplifying a target sequence by reacting nucleic acid extracted in step (a) for less than ten minutes with a reaction mixture comprising a strand displacement DNA polymerase and a sequence specific LAMP primer set, and (c) detecting the presence or absence of an amplified product of step (b); wherein the presence of said amplification product is indicative of the presence of SARS-CoV-2 in the test sample. In some implementations, the amplifying step comprises reacting the nucleic acid extracted in step (a) with a reaction mixture comprising a strand displacement DNA polymerase and a sequence-specific primer set, wherein said sequence-specific primer set is selected from the group consisting of Set-1 through Set-17. In such implementations, detecting the presence or absence of the amplification product can comprise hybridizing the amplified product with a molecular beacon comprising a polynucleotide sequence selected from the group consisting of nucleotides 5-27 of SEQ ID NO.: 55, nucleotides 7-25 of SEQ ID NO.: 56, nucleotides 5-22 of SEQ ID NO.: 75, nucleotides 5-22 of SEQ ID NO.: 76, nucleotides 5-29 of SEQ ID NO.: 77, nucleotides 6-26 of SEQ ID NO.: 78, nucleotides 5-29 of SEQ ID NO.: 79, nucleotides 5-22 of SEQ ID NO.: 80, nucleotides 5-22 of SEQ ID NO.: 81, nucleotides 4-22 of SEQ ID NO.: 82, nucleotides 6-28 of SEQ ID NO.: 83, nucleotides 6-25 of SEQ ID NO.: 84, nucleotides 3-23 of SEQ ID NO.: 85, and nucleotides 2-24 of SEQ ID NO.: 95. In such implementations, detecting the presence or absence of the amplification product can comprise hybridizing the amplified product with a molecular beacon consisting of a polynucleotide sequence selected from the group consisting of SEQ ID NO.: 55, SEQ ID NO.: 56, SEQ ID NOS.: 75 through 85, and SEQ ID NO.: 95.

In certain implementations of the method to detect SARS-CoV-2 in a test sample, the set of polynucleotides is Set-1 or Set-4, and the labeled polynucleotide comprises nucleotides 5-27 of SEQ ID NO.: 55. More preferably, the sequence of the labeled polynucleotides is SEQ ID NO.: 55. In implementations wherein the set of polynucleotides is Set-3 or Set-8, the labeled polynucleotide comprises nucleotides 7-25 of SEQ ID NO.: 56. More preferably, the sequence of the labeled polynucleotides is SEQ ID NO.: 56. In implementations, wherein the set of polynucleotides is Set-5 or Set-9, the labeled polynucleotide comprises a sequence selected from the group consisting of nucleotides 5-22 of SEQ ID NO.: 75, nucleotides 5-22 of SEQ ID NO.: 76, nucleotides 5-22 of SEQ ID NO.: 80, nucleotides 5-22 of SEQ ID NO.: 81, nucleotides 4-22 of SEQ ID NO.: 82, nucleotides 6-28 of SEQ ID NO.: 83, nucleotides 6-25 of SEQ ID NO.: 84, nucleotides 3-23 of SEQ ID NO.: 85. More preferably, the sequence of the labeled polynucleotide is selected from the group consisting of SEQ ID NO.: 75, SEQ ID NO.: 76, SEQ ID NO.: 80, SEQ ID NO.: 82, SEQ ID NO.: 83, SEQ ID NO.: 84, and SEQ ID NO.: 85. In implementations wherein the set of polynucleotides is Set-9, the sequence of the labeled polynucleotide preferably is SEQ ID NO.: 83. In implementations wherein the set of polynucleotides is Set-11 or Set-13, the labeled polynucleotide comprises a sequence selected from the group consisting of nucleotides 5-29 of SEQ ID NO.: 77 and nucleotides 5-29 of SEQ ID NO.: 79. Preferably, the labeled polynucleotide comprises SEQ ID NO.: 77 or SEQ ID NO.: 79. In implementations, wherein the set of polynucleotides is Set-12, the labeled polynucleotide comprises nucleotides 6-26 of SEQ ID NO.: 78. Preferably, the sequence of the labeled polynucleotides is SEQ ID NO.: 78. In implementations wherein the set of polynucleotides is selected from the group consisting of Set-14, Set-15, Set-16 and Set-17, the labeled polynucleotide comprises nucleotides 2-24 of SEQ ID NO.: 95. More preferably, the sequence of the labeled polynucleotides is SEQ ID NO.: 95.

Yet another aspect of the invention provides kits comprising the compositions comprising a set of polynucleotides selected from the group consisting Set-1 through Set-17. In some embodiments, the kit further comprises a strand displacement polymerase and a reverse transcriptase. In certain embodiments, the kit comprises a molecular beacon comprising a fluorophore, a quencher, and a polynucleotide, wherein the polynucleotide comprises a sequence selected from the group consisting of nucleotides 5-27 of SEQ ID NO.: 55, nucleotides 7-25 of SEQ ID NO.: 56, nucleotides 5-22 of SEQ ID NO.: 75, nucleotides 5-22 of SEQ ID NO.: 76, nucleotides 5-29 of SEQ ID NO.: 77, nucleotides 6-26 of SEQ ID NO.: 78, nucleotides 5-29 of SEQ ID NO.: 79, nucleotides 5-22 of SEQ ID NO.: 80, nucleotides 5-22 of SEQ ID NO.: 81, nucleotides 4-22 of SEQ ID NO.: 82, nucleotides 6-28 of SEQ ID NO.: 83, nucleotides 6-25 of SEQ ID NO.: 84, nucleotides 3-23 of SEQ ID NO.: 85, and nucleotides 2-24 of SEQ ID NO.: 95. The polynucleotide sequence of the molecular beacon can comprise a sequence selected from the group consisting of SEQ ID NO.: 55, SEQ ID NO.: 56, SEQ ID NOS.: 75 through 85, and SEQ ID NO.: 95. In some embodiments, the polynucleotide sequence of the molecular beacon consists of a sequence selected from the group consisting of SEQ ID NO.: 55, SEQ ID NO.: 56, SEQ ID NOS.: 75 through 85, and SEQ ID NO.: 95.

In certain implementations of the kit, the set of polynucleotides is Set-1 or Set-4. In such implementation, the kit can further comprise a molecular beacon comprising a fluorophore, a quencher, and a polynucleotide, wherein the polynucleotide comprises nucleotides 5-27 of SEQ ID NO.: 55. Preferably, the polynucleotide of the molecular beacon consists of SEQ ID NO.: 55. In other implementations of the kit, the set of polynucleotides is selected from the group consisting of Set-3 and Set-8. In such implementations, the kit can further comprise a molecular beacon comprising a fluorophore, a quencher, and a polynucleotide, wherein the polynucleotide comprises nucleotides 7-25 of SEQ ID NO.: 56. Preferably, the polynucleotide of the molecular beacon consists of SEQ ID NO.: 56. In yet another implementation of the kit, the set of polynucleotides is selected from the group consisting of Set-5 and Set-9. In such implementations, the kit can further comprise a molecular beacon comprising a fluorophore, a quencher, and a polynucleotide, wherein the polynucleotide comprises a sequence selected from the group consisting of nucleotides 5-22 of SEQ ID NO.: 75, nucleotides 5-22 of SEQ ID NO.: 76, nucleotides 5-22 of SEQ ID NO.: 80, nucleotides 5-22 of SEQ ID NO.: 81, nucleotides 4-22 of SEQ ID NO.: 82, nucleotides 6-28 of SEQ ID NO.: 83, nucleotides 6-25 of SEQ ID NO.: 84, and nucleotides 3-23 of SEQ ID NO.: 85. Preferably, the polynucleotide of the molecular beacon consists of a sequence selected from the group consisting of SEQ ID NO.: 75, SEQ ID NO.: 76, SEQ ID NO.: 80, SEQ ID NO.: 81, SEQ ID NO.: 82, SEQ ID NO.: 83, SEQ ID NO.: 84, and SEQ ID NO.: 85. In other implementations of the kit, the set of polynucleotides is selected from the group consisting of Set-11 and Set-13. In such implementations, the kit can further comprise a molecular beacon comprising a fluorophore, a quencher, and a polynucleotide, wherein the polynucleotide comprises a sequence selected from the group consisting of nucleotides 5-29 of SEQ ID NO.: 77 and nucleotides 5-29 of SEQ ID NO.: 79. Preferably, the polynucleotide of the molecular beacon consists of a sequence selected from the group consisting of SEQ ID NO.: 77 and SEQ ID NO.: 79. In yet another implementation of the kit, the set of polynucleotides is Set-12. In such implementations, the kit can further comprise a molecular beacon comprising a fluorophore, a quencher, and a polynucleotide, wherein the polynucleotide comprises nucleotides 6-26 of SEQ ID NO.: 78. Preferably, the polynucleotide of the molecular beacon consists of SEQ ID NO.: 78. In certain implementations of the kit, the set of polynucleotides is selected from the group consisting of Set-14, Set-15, Set-16, and Set-17. In such implementations, the kit can further comprise a molecular beacon comprising a fluorophore, a quencher, and a polynucleotide comprising nucleotides 2-24 of SEQ ID NO.: 95. Preferably, the polynucleotide of the molecular beacon consists of SEQ ID NO.: 95.

Another aspect of the invention provides a kit comprising a set of polynucleotides comprising SEQ ID NO.: 49, SEQ ID NO.: 50, SEQ ID NO.: 51, SEQ ID NO.: 52, SEQ ID NO.: 53, and SEQ ID NO.: 54. The kit preferably, further comprises a strand displacement polymerase and reverse transcriptase. In some implementations, the kit further comprises a molecular beacon comprising a fluorophore, a quencher, and SEQ ID NO. 83. In another implementation, the kit further comprises a set of polynucleotides comprising SEQ ID NO.: 63, SEQ ID NO.: 64, SEQ ID NO.: 65, SEQ ID NO.: 66, SEQ ID NO.: 67, and SEQ ID NO.: 68. This kit preferably further comprises a molecular beacon comprising a fluorophore, a quencher and SEQ ID NO. 77.

DETAILED DESCRIPTION

The present invention encompasses, in some embodiments, a composition comprising a set of polynucleotides for priming a nucleic acid amplification reaction and methods of using such. In some embodiments, the composition further comprises a probe.

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded. The term "nucleic acid" refers to nucleotides and nucleosides which make up, for example, deoxyribonucleic acid (DNA) macromolecules and ribonucleic acid (RNA) macromolecules. The most common nucleic acids are deoxyribonucleic acid (DNA) and ribonucleic acid (RNA). It should be further understood that the present invention can be used for biological sequences containing artificial nucleotides such as peptide nucleic acid (PNA), morpholino, locked nucleic acid (LNA), glycol nucleic acid (GNA) and threose nucleic acid (TNA), among others. Preferably, the artificial nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides, containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)).

As used herein, a "polynucleotide" refers to a polymeric chain containing two or more nucleotides, which contain deoxyribonucleotides, ribonucleotides, and/or their analog, such as those containing modified backbones (e.g. peptide nucleic acids (PNAs) or phosphorothioates) or modified bases. "Polynucleotides" includes primers, oligonucleotides, nucleic acid strands, etc. A polynucleotide may contain standard or non-standard nucleotides. Thus, the term includes mRNA, tRNA, rRNA, ribozymes, DNA, cDNA, recombinant nucleic acids, branched nucleic acids, plasmids, vectors, probes, primers, etc. Typically, a polynucleotide contains a 5' phosphate at one terminus ("5' terminus") and a 3' hydroxyl group at the other terminus ("3' terminus") of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide. Where nucleic acid of the invention takes the form of RNA, it may or may not have a 5' cap.

LAMP is a nucleic acid amplification method that relies on auto-cycle strand-displacement DNA synthesis performed by Bst DNA polymerase, or other strand displacement polymerases. The amplified products are stem-loop structures with several repeated sequences of the target and have multiple loops. The principal merit of this method is that denaturation of the DNA template is not required, and thus the LAMP reaction can be conducted under isothermal conditions (ranging from 60 to 67° C.). LAMP requires only one enzyme and four types of primers that recognize six distinct hybridization sites in the target sequence. The reaction can be accelerated by the addition of two additional primers. The method produces a large amount of amplified product, resulting in easier detection, such as detection by visual judgment of the turbidity or fluorescence of the reaction mixture.

In brief, the reaction is initiated by annealing and extension of a pair of 'loop-forming' primers (forward and backward inner primers, FIP and BIP, respectively), followed by annealing and extension of a pair of flanking primers (F3 and B3). Extension of these primers results in strand-displacement of the loop-forming elements, which fold up to form terminal hairpin-loop structures. Once these key structures have appeared, the amplification process becomes self-sustaining, and proceeds at constant temperature in a continuous and exponential manner (rather than a cyclic manner, like PCR) until all of the nucleotides (dATP, dTTP, dCTP & dGTP) in the reaction mixture have been incorporated into the amplified DNA. Optionally, an additional pair of primers can be included to accelerate the reaction. These primers, termed Loop primers, hybridize to non-inner primer bound terminal loops of the inner primer dumbbell shaped products.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

Applications for LAMP have been further extended to include detection of RNA molecules by addition of Reverse Transcriptase enzyme (RT). By including RNA detection, the types of targets for which LAMP can be applied are also expanded and add the ability to additionally target RNA based viruses, important regulatory non-coding RNA (sRNA, miRNA), and RNA molecules that have been associated with particular disease or physiological states. The ability to detect RNA also has the potential to increase assay sensitivity, for instance in choosing highly expressed, stable, and/or abundant messenger RNA (mRNA) or ribosomal RNA (rRNA) targets. This preliminary phase of amplification involves the reverse transcription of RNA molecules to complementary DNA (cDNA). The cDNA then serves as template for the strand displacing DNA polymerase. Use of a thermostable RT enzyme (i.e., NEB RTx) enables the reaction to be completed at a single temperature and in a one step, single mix reaction.

A "target sequence," as used herein, means a nucleic acid sequence of *Neisseria gonorrhoeae*, or complement thereof, that is amplified, detected, or both amplified and detected using one or more of the polynucleotides herein provided. Additionally, while the term target sequence sometimes refers to a double stranded nucleic acid sequence, those skilled in the art will recognize that the target sequence can also be single stranded, e.g., RNA. A target sequence may be selected that is more or less specific for a particular organism. For example, the target sequence may be specific to an entire genus, to more than one genus, to a species or subspecies, serogroup, auxotype, serotype, strain, isolate or other subset of organisms.

The speed, specificity and sensitivity of the primers/probe compositions and method described herein result from several aspects. Exemplary primers for use in the compositions and methods according to the present invention include those provided in Table 1.

TABLE 1

Primer Sequences

| Sequence ID | Target | Sequence (5' to 3') |
|---|---|---|
| SEQ ID No.: 1 | N gene | GGACCAGGAACTAATCAGACA |
| SEQ ID No.: 2 | N gene | TCTGCGGTAAGGCTTGAG |
| SEQ ID No.: 3 | N gene | ACCACGTTCCCGAAGGTGTCAGCGTTCTTCGGAATGTC |
| SEQ ID No.: 4 | N gene | TGACCTACACAGGTGCCATCAAGGCTCTGTTGGTGGGAAT |
| SEQ ID No.: 5 | N gene | GACTTCCATGCCAATGCG |
| SEQ ID No.: 6 | N gene | GCTGAATAAGCATATTGACGCATAC |
| SEQ ID No.: 7 | N gene | ACCCCAAAATCAGCGAAA |
| SEQ ID No.: 8 | N gene | ATTGGAACGCCTTGTCC |
| SEQ ID No.: 9 | N gene | ATCGCGCCCCACTGCCACCCCGCATTACGTTT |
| SEQ ID No.: 10 | N gene | CGTCGGCCCCAAGGTTTATCCTTGCCATGTTGAGTG |
| SEQ ID No.: 11 | N gene | CAGTTGAATCTGAGGGTCCA |
| SEQ ID No.: 12 | N gene | GTCTTGGTTCACCGCTCT |
| SEQ ID No.: 13 | N gene | AAAAGGCTTCTACGCAGAA |
| SEQ ID No.: 14 | N gene | CCTTTACCAGACATTTTGCTC |
| SEQ ID No.: 15 | N gene | ACTGCTGCCTGGAGTTGAATCAGTCAAGCCTCTTCTCG |
| SEQ ID No.: 16 | N gene | CTGCTAGAATGGCTGGCAATGTGGTTCAATCTGTCAAGCA |
| SEQ ID No.: 17 | N gene | ACTGTTGCGACTACGTGAT |
| SEQ ID No.: 18 | N gene | GCGGTGATGCTGCTCT |
| SEQ ID No.: 19 | N gene | AGGAACTGATTACAAACATTGG |
| SEQ ID No.: 20 | N gene | TTTTGTATGCGTCAATATGCTT |
| SEQ ID No.: 21 | N gene | AAGGTGTGACTTCCATGCCAACAATTTGCCCCCAGC |
| SEQ ID No.: 22 | N gene | GGGAACGTGGTTGACCTACAGACTTGATCTTTGAAATTTGGATC |
| SEQ ID No.: 23 | N gene | TGCGCGACATTCCGAA |
| SEQ ID No.: 24 | N gene | GGTGCCATCAAATTGGATGA |
| SEQ ID No.: 25 | N gene | TCAAAGATCAAGTCATTTTGCT |
| SEQ ID No.: 26 | N gene | GCCTGAGTTGAGTCAGC |
| SEQ ID No.: 27 | N gene | GTCTCTGCGGTAAGGCTTGAATACAAAACATTCCCACCAAC |
| SEQ ID No.: 28 | N gene | GCAAACTGTGACTCTTCTTCCTGTGCTCATGGATTGTTGCA |

TABLE 1-continued

Primer Sequences

| Sequence ID | Target | Sequence (5' to 3') |
|---|---|---|
| SEQ ID No.: 29 | N gene | ATCAGCCTTCTTCTTTTTGTCC |
| SEQ ID No.: 30 | N gene | TGCAGATTTGGATGATTTCTCC |
| SEQ ID No.: 31 | ORF1ab | CAGAAATCAATACTGAGTCCTCT |
| SEQ ID No.: 32 | ORF1ab | GTAGCCAAATCAGATGTGAAC |
| SEQ ID No.: 33 | ORF1ab | CACAGAATTTTGAGCAGTTTCAAGAGTTCAGAGGCTGCTCGTG |
| SEQ ID No.: 34 | ORF1ab | CGTGTTTTACAGAAGGCCGCCATAGCATCAATGAGTCTCAGT |
| SEQ ID No.: 35 | ORF1ab | GCGGGAGAAAATTGATCGTAC |
| SEQ ID No.: 36 | ORF1ab | ATAACAATACTAGATGGAATTTCACAGT |
| SEQ ID No.: 37 | ORF1ab | CAAATTGTTGAATCCTGTGGT |
| SEQ ID No.: 38 | ORF1ab | AAATTCCATCTAGTATTGTTATAGCG |
| SEQ ID No.: 39 | ORF1ab | AATGCATAAAGAGGACTCAGTATTGATTTCAATTTTAAAGTTACAAAAGGAAAAGCT |
| SEQ ID No.: 40 | ORF1ab | CAGAGGCTGCTCGTGTTGTCACGCACAGAATTTTGAGC |
| SEQ ID No.: 41 | ORF1ab | TGTTCACCAATATTCCAGGCA |
| SEQ ID No.: 42 | ORF1ab | CGATCAATTTTCTCCCGCAC |
| SEQ ID No.: 43 | N gene | GTCAAGCCTCTTCTCGTTC |
| SEQ ID No.: 44 | N gene | CTTAGTGACAGTTTGGCCTT |
| SEQ ID No.: 45 | N gene | CCGCCATTGCCAGCCAAACAGTTCAAGAAATTCAACTCC |
| SEQ ID No.: 46 | N gene | GATGCTGCTCTTGCTTTGCTGGCCTTTACCAGACATTTTGC |
| SEQ ID No.: 47 | N gene | GAGAAGTTCCCCTACTGCTG |
| SEQ ID No.: 48 | N gene | TGACAGATTGAACCAGCTTGA |
| SEQ ID No.: 49 | N gene | AATTTCAAAGATCAAGTCATTTTGC |
| SEQ ID No.: 50 | N gene | GTTGAGTCAGCACTGCTC |
| SEQ ID No.: 51 | N gene | AGGCTTGAGTTTCATCAGCCTCGCATACAAAACATTCCCAC |
| SEQ ID No.: 52 | N gene | GCAGAGACAGAAGAAACAGCAAACATTGTTGCAATTGTTTGGAGAA |
| SEQ ID No.: 53 | N gene | TCTTTTTGTCCTTTTTAGGCTCTG |
| SEQ ID No.: 54 | N gene | CTCTTCTTCCTGCTGCAGATTTGG |
| SEQ ID No.: 57 | ORF1ab | CAAATTGTTGAATCCTGTGGT |
| SEQ ID No.: 58 | ORF1ab | AAATTCCATCTAGTATTGTTATAGCG |
| SEQ ID No.: 59 | ORF1ab | AATGCATAAAGAGGACTCAGTATTGATTTCAATTTTAAAGTTACAAAAGGAAAAGCT |
| SEQ ID No.: 60 | ORF1ab | CAGAGGCTGCTCGTGTTGTCACGCACAGAATTTTGAGC |
| SEQ ID No.: 61 | ORF1ab | TGTTCACCAATATTCCAGGCA |
| SEQ ID No.: 62 | ORF1ab | CGATCAATTTTCTCCCGCAC |
| SEQ ID No.: 63 | ORF1ab | TCTTATCAGAGGCACGTCA |
| SEQ ID No.: 64 | ORF1ab | TGTCTCACCACTACGACC |
| SEQ ID No.: 65 | ORF1ab | ACGTTTGATGAACACATAGGGCTTAAAGATGGCACTTGTGGC |
| SEQ ID No.: 66 | ORF1ab | TCGGATGCTCGAACTGCACTGCCTTCGAGTTCTGCTA |
| SEQ ID No.: 67 | ORF1ab | TTCAAGTTGAGGCAAAACGC |
| SEQ ID No.: 68 | ORF1ab | CATGGTCATGTTATGGTTGAGC |

TABLE 1-continued

Primer Sequences

| Sequence ID | Target | Sequence (5' to 3') |
|---|---|---|
| SEQ ID No.: 69 | ORF1ab | ATGTCCAAATTTTGTATTTCCCTT |
| SEQ ID No.: 70 | ORF1ab | GCTTTAACAAAATCGCCCG |
| SEQ ID No.: 71 | ORF1ab | GCAACTGGATAGACAGATCGAATTCTATCCATAATCAAGACTATTCAACCA |
| SEQ ID No.: 72 | ORF1ab | CACCAAATGAATGCAACCAAATGTGTCTGCCATGAAGTTTCACC |
| SEQ ID No.: 73 | ORF1ab | CATCAAGCTTTTTCTTTTCAACCC |
| SEQ ID No.: 74 | ORF1ab | CCTTTCAACTCTCATGAAGTGTG |
| SEQ ID No.: 86 | ORF1ab | GAGGGACAAGGACACCAAG |
| SEQ ID No.: 87 | ORF1ab | TCGGATGCTCGAACTGCACTGTCTCACCACTACGACC |
| SEQ ID No.: 88 | ORF1ab | GGTAGCAGAACTCGAAGGCAT |
| SEQ ID No.: 89 | E gene | AAGAGACAGGTACGTTAATAGT |
| SEQ ID No.: 90 | E gene | TTAGACCAGAAGATCAGGAAC |
| SEQ ID No.: 91 | E gene | AAGCGCAGTAAGGATGGCTATAGCGTACTTCTTTTTCTTGC |
| SEQ ID No.: 92 | E gene | TGCGTACTGCTGCAATATTGTTTTAACACGAGAGTAAACGTAAA |
| SEQ ID No.: 93 | E gene | TGTAACTAGCAAGAATACCACG |
| SEQ ID No.: 94 | E gene | CGTGAGTCTTGTAAAACCTTCT |
| SEQ ID No.: 96 | E gene | GAAGATCAGGAACTCTAGAAGA |
| SEQ ID No.: 97 | E gene | ACACAATCGAAGCGCAGTAAGTTTTCTTGCTTTCGTGGTAT |
| SEQ ID No.: 98 | E gene | GCGTACTGCTGCAATATTGTTTTAACACGAGAGTAAACGTAAA |
| SEQ ID No.: 99 | E gene | TGGCTAGTGTAACTAGCAAGA |
| SEQ ID No.: 100 | E gene | ACGTTAATAGTTAATAGCGTACTT |
| SEQ ID No.: 101 | E gene | TCAGGAACTCTAGAAGAATTCA |
| SEQ ID No.: 102 | E gene | ACAATCGAAGCGCAGTAAGGTTTTCTTGCTTTCGTGGTAT |
| SEQ ID No.: 103 | E gene | TGCGTACTGCTGCAATATTGTTTTAACACGAGAGTAAACGTAAA |

Detection of the LAMP amplified products can be achieved via a variety of methods. In some implementations, LAMP amplified products are detected using intercalating dyes. Intercalating dyes are generally aromatic cations with planar structures that insert between stacked base pairs in the DNA duplex, an arrangement that provides an environmentally dependent fluorescence enhancement for dye molecules and creates a large increase in the fluorescence signal relative to the free dye in solution. The signal enhancement provides a proportional response, allowing direct quantitative DNA measurements. Preferred intercalating dyes in the present disclosure include fluorescent dyes. The dye can be a cyanine or a non-cyanine intercalating die. In some cases, the intercalating dye is a cyanine dye. In some cases, the cyanine dye can be Thiazole Orange, SYBR® (e.g. Sybr Green I, Sybr Green II, Sybr Gold, SYBR DX), Oil Green, CyQuant GR, SYTOX Green, SYTO9, SYTO10, SYTO17, SYBR14, Oxazile Yellow, Thiazone Orange, SYTO, TOTO, YOYO, BOBO, and POPO. In some cases, the dye is a non-cyanine dye. In some cases, the non cyanine dye is pentacene, anthracene, naphthalene, ferrocene, methyl viologen, tri-morpholino ammonium, propidium (e.g., propidium iodide) or another aromatic or heteroaromatic derivative.

In a preferred embodiment, detection of product is conducted by adding a fluorescently-labeled probe to the primer mix. The term used herein "probe" refers to a single-stranded nucleic acid molecule comprising a portion or portions that are complementary, or substantially complementary, to a target sequence. In certain implementations, the fluorescently-labeled probe is a molecular beacon.

As used herein, "molecular beacon" refers to a single stranded hairpin-shaped oligonucleotide probe designed to report the presence of specific nucleic acids in a solution. A molecular beacon consists of four components; a stem, hairpin loop, end labelled fluorophore and opposite end-labelled quencher (Tyagi et al., (1998) Nature Biotechnology 16:49-53). When the hairpin-like beacon is not bound to a target, the fluorophore and quencher lie close together and fluorescence is suppressed. In the presence of a complementary target nucleotide sequence, the stem of the beacon opens to hybridize to the target. This separates the fluorophore and quencher, allowing the fluorophore to fluoresce. Alternatively, molecular beacons also include fluorophores that emit in the proximity of an end-labelled donor. "Wavelength-shifting Molecular Beacons" incorporate an additional harvester fluorophore enabling the fluorophore to emit more strongly. Current reviews of molecular beacons include Wang et al., 2009, Angew Chem Int Ed Engl, 48(5):856-870; Cissell et al., 2009, Anal Bioanal Chem 393(1):125-35; Li et al., 2008, Biochem Biophys Res Comm 373(4):457-61; and Cady, 2009, Methods Mol Biol 554:367-79. Exemplary probes for use in the compositions and methods according to the present invention include those provided in Table 2. In certain implementations, the probes may include one or more linked nucleic acids (LNA) as indicated by "[+X]", where X indicates the identity of the nucleobase. Bold indicates the portion of the molecular beacon that hybridizes to sequences found in the target coronavirus genome.

can comprise a sequence selected from the group consisting of SEQ ID NO.: 55, SEQ ID NO.: 56 and SEQ ID NOS.: 75-85. More preferably, polynucleotide sequence of the molecular beacon consists of a sequence selected from the group consisting of SEQ ID NO.: 55, SEQ ID NO.: 56 and SEQ ID NOS.: 75-85.

The term "label" as used herein means a molecule or moiety having a property or characteristic which is capable of detection and, optionally, of quantitation. A label can be directly detectable, as with, for example (and without limitation), radioisotopes, fluorophores, chemiluminophores, enzymes, colloidal particles, fluorescent microparticles and the like; or a label may be indirectly detectable, as with, for

TABLE 2

Probe Sequences

| ID | Fluor | Quench | Sequence (5' to 3') | Sequence ID |
|---|---|---|---|---|
| MB1 | FAM | BHQ1 | CACGCCAAA[+T]TT[+C]AAA[+G]AT[+C]AAGTCATGGCGTG | SEQ ID NO.: 55 |
| MB2 | FAM | BHQ1 | CAGCTGCTTGA[+C]AGA[+T]TGA[+A]CCAGCAGCTG | SEQ ID NO.: 56 |
| MB3 | FAM | BHQ1 | CACGGTGACT[+C]TT[+C]TT[+C]CTGCTCACCGTG | SEQ ID NO.: 75 |
| MB4 | FAM | BHQ1 | CGAGTCCTGC[+T]GC[+A]GA[+T]TTGGACTCG | SEQ ID NO.: 76 |
| MB5 | FAM | BHQ1 | CAGCTCATGG[+T]CAT[+G]TTAT[+G]GTTGAGCTG | SEQ ID NO.: 77 |
| MB6 | FAM | BHQ1 | <u>CACACTTT[+C]AA[+C]TC[+T]CA[+T]GAAGTGTG</u> | SEQ ID NO.: 78 |
| MB7 | FAM | BHQ1 | CAGCTCATGGTCATGTTATGGTTGAGCTG | SEQ ID NO.: 79 |
| MB8 | FAM | BHQ1 | <u>CGAGTCCTGC[+T]GC[+A]GA[+T]TTGGACTCG</u> | SEQ ID NO.: 80 |
| MB9 | FAM | BHQ1 | <u>CATGTCCTGC[+T]GC[+A]GA[+T]TTGGACATG</u> | SEQ ID NO.: 81 |
| MB10 | FAM | BHQ1 | <u>CACTTCCTGC[+T]GC[+A]GA[+T]TTGGAAGTG</u> | SEQ ID NO.: 82 |
| MB11 | FAM | BHQ1 | CACGCGTGACT[+C]TTCTT[+C]CTGC[+T]GCAGACGCGTG | SEQ ID NO.: 83 |
| MB12 | FAM | BHQ1 | CACGCTTC[+T]TC[+C]TGC[+T]GC[+A]GA[+T]TTGAAGCGTG | SEQ ID NO.: 84 |
| MB13 | FAM | BHQ1 | CAGACTCTTCT[+T]CC[+T]GC[+T]GCAGAGTCTG | SEQ ID NO.: 85 |
| MB14 | FAM | BHQ1 | CACGTGAGT[+C]TT[+G]TAA[+A]ACC[+T]TCTCACGTG | SEQ ID NO.: 95 |

In one implementation, the molecular beacon comprises a fluorophore, a quencher, and a polynucleotide, wherein the polynucleotide comprises a sequence selected from the group consisting of nucleotides 5-27 of SEQ ID NO.: 55, nucleotides 7-25 of SEQ ID NO.: 56, nucleotides 5-22 of SEQ ID NO.: 75, nucleotides 5-22 of SEQ ID NO.: 76, nucleotides 5-29 of SEQ ID NO.: 77, nucleotides 6-26 of SEQ ID NO.: 78, nucleotides 5-29 of SEQ ID NO.: 79, nucleotides 5-22 of SEQ ID NO.: 80, nucleotides 5-22 of SEQ ID NO.: 81, nucleotides 4-22 of SEQ ID NO.: 82, nucleotides 6-28 of SEQ ID NO.: 83, nucleotides 6-25 of SEQ ID NO.: 84, nucleotides 3-23 of SEQ ID NO.: 85. In one embodiment, the polynucleotide comprises a sequence selected from the group consisting of SEQ ID NO.: 55, SEQ ID NO.: 56 and SEQ ID NOS.: 75-85. In another embodiment, the polynucleotide consists of a sequence selected from the group consisting of SEQ ID NO.: 55, SEQ ID NO.: 56 and SEQ ID NOS.: 75-85.

The molecular beacon is preferably used in a composition also comprising a set of sequence-specific LAMP primers. In one implementation, the molecular beacon comprises a sequence selected from the group consisting of nucleotides 5-27 of SEQ ID NO.: 55 and nucleotides 7-25 of SEQ ID NO.: 56. In such an implementation, the molecular beacon example, specific binding members. It will be understood that directly detectable labels may require additional components such as, for example, substrates, triggering reagents, quenching moieties, light, and the like to enable detection and/or quantitation of the label. When indirectly detectable labels are used, they are typically used in combination with a "conjugate". A conjugate is typically a specific binding member that has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

The molecular beacon can be composed of nucleic acid only such as DNA or RNA, or it can be composed of a peptide nucleic acid (PNA) conjugate. The fluorophore can be any fluorescent organic dye or a single quantum dot. The quenching moiety desirably quenches the luminescence of the fluorophore. Any suitable quenching moiety that quenches the luminescence of the fluorophore can be used. A fluorophore can be any fluorescent marker/dye known in the art. Examples of suitable fluorescent markers include, but are not limited to, Fam, Hex, Tet, Joe, Rox, Tamra, Max, Edans, Cy dyes such as Cy5, Fluorescein, Coumarin, Eosine, Rhodamine, Bodipy, Alexa, Cascade Blue, Yakima Yellow, Lucifer Yellow, Texas Red, and the family of ATTO dyes. A quencher can be any quencher known in the art. Examples of quenchers include, but are not limited to, DABCYL (4-(dimethylaminoazo)benzene-4-carboxylic acid), dark quenchers such as ECLIPSE Dark Quencher, ElleQuencher, Tamra (tetramethylrhodamine), Black Hole quenchers and QSY dyes. The skilled person would know which combinations of dye/quencher are suitable when designing a probe. In an exemplary embodiment, fluorescein (FAM) is used in conjunction with Blackhole Quencher™ (BHQ™) Binding of the molecular beacon to amplified product can then be directly, visually assessed. Alternatively, the fluorescence level can be measured by spectroscopy in order to improve sensitivity.

A variety of commercial suppliers produce standard and custom molecular beacons, including Abingdon Health (UK; abingdonhealth.com), Attostar (US, MN; attostar.com), Biolegio (NLD; biolegio.com), Biomers.net (DEU; biomers.net), Biosearch Technologies (US, CA; biosearchtech.com), Eurogentec (BEL; eurogentec.com), Gene Link (US, NY; genelink.com) Integrated DNA Technologies (US, IA; idtdna.com), Isogen Life Science (NLD; isogen-lifescience.com), Midland Certified Reagent (US, TX; oligos.com), Eurofins (DEU; eurofinsgenomics.eu), Sigma-Aldrich (US, TX; sigmaaldrich.com), Thermo Scientific (US, MA; thermoscientific.com), TIB MOLBIOL (DEU; tib-molbiol.de), TriLink Bio Technologies (US, CA; trilinkbiotech.com). A variety of kits, which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com).

The oligonucleotide probes and primers of the invention are optionally prepared using essentially any technique known in the art. In certain embodiments, for example, the oligonucleotide probes and primers described herein are synthesized chemically using essentially any nucleic acid synthesis method, including, e.g., according to the solid phase phosphoramidite triester method described by Beaucage and Caruthers (1981), Tetrahedron Letts. 22(20): 1859-1862, which is incorporated by reference, or another synthesis technique known in the art, e.g., using an automated synthesizer, as described in Needham-VanDeventer et al. (1984) Nucleic Acids Res. 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids described herein optionally include various modifications. To further illustrate, primers are also optionally modified to improve the specificity of amplification reactions as described in, e.g., U.S. Pat. No. 6,001,611, issued Dec. 14, 1999, which is incorporated by reference. Primers and probes can also be synthesized with various other modifications as described herein or as otherwise known in the art.

In addition, essentially any nucleic acid (and virtually any labeled nucleic acid, whether standard or non-standard) can be custom or standard ordered from any of a variety of commercial sources, such as Integrated DNA Technologies, the Midland Certified Reagent Company, Eurofins, Biosearch Technologies, Sigma Aldrich and many others.

The term "test sample" as used herein, means a sample taken from an organism or biological fluid that is suspected of containing or potentially contains a target sequence. The test sample can be taken from any biological source, such as for example, tissue, blood, saliva, sputa, mucus, sweat, urine, urethral swabs, cervical swabs, vaginal swabs, urogenital or anal swabs, conjunctival swabs, ocular lens fluid, cerebral spinal fluid, milk, ascites fluid, synovial fluid, peritoneal fluid, amniotic fluid, fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma or serum from blood, disrupting cells or viral particles, preparing liquids from solid materials, diluting viscous fluids, filtering liquids, distilling liquids, concentrating liquids, inactivating interfering components, adding reagents, purifying nucleic acids, and the like.

Advantageously, the invention enables reliable rapid detection of SARS-CoV-2 in a clinical sample, such as sputum or a nasal or pharyngeal swab.

To further illustrate, prior to analyzing the target nucleic acids described herein, those nucleic acids may be purified or isolated from samples that typically include complex mixtures of different components. Cells in collected samples are typically lysed to release the cell contents, including target nucleic acids. For example, a test sample suspected of containing virus, can be lysed by contacting viral particles with various enzymes, chemicals, and/or lysed by other approaches known in the art, which degrade, e.g., viral particle walls. In some embodiments, nucleic acids are analyzed directly in the cell lysate. In other embodiments, nucleic acids are further purified or extracted from lysates prior to detection. Essentially any nucleic acid extraction methods can be used to purify nucleic acids in the samples utilized in the methods of the present invention. Exemplary techniques that can be used to purifying nucleic acids include, e.g., affinity chromatography, hybridization to probes immobilized on solid supports, liquid-liquid extraction (e.g., phenol-chloroform extraction, etc.), precipitation (e.g., using ethanol, etc.), extraction with filter paper, extraction with micelle-forming reagents (e.g., cetyl-trimethyl-ammonium-bromide, etc.), binding to immobilized intercalating dyes (e.g., ethidium bromide, acridine, etc.), adsorption to silica gel or diatomic earths, adsorption to magnetic glass particles or organo silane particles under chaotropic conditions, and/or the like. Sample processing is also described in, e.g., U.S. Pat. Nos. 5,155,018, 6,383,393, and 5,234,809, which are each incorporated by reference.

A test sample may optionally have been treated and/or purified according to any technique known by the skilled person, to improve the amplification efficiency and/or qualitative accuracy and/or quantitative accuracy. The sample may thus exclusively, or essentially, consist of nucleic acid(s), whether obtained by purification, isolation, or by chemical synthesis. Means are available to the skilled person, who would like to isolate or purify nucleic acids, such as DNA, from a test sample, for example to isolate or purify DNA from pharyngeal scrapes (e.g., QIAamp-DNA Mini-Kit; Qiagen, Hilden, Germany).

EQUIVALENTS AND SCOPE

Those skilled in the art will recognize or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Target Selection and Primer Probe Design

Gene sequences for multiple isolates of SARS-CoV-2, closely related species such as common human coronavirus, severe acute respiratory syndrome (SARS)-related coronavirus, and Middle East respiratory syndrome-related coronavirus (MERS-CoV), and for other species commonly found in the nasal or pharyngeal samples acquired from patients with upper respiratory symptoms were retrieved from the NCBI database. Sequences were aligned using Clustal omega (Sievers, et al. 2011. Molecular Systems Biology 7:539) and regions with unique specific bases to SARS-CoV-2 species were identified. Loop mediated amplification primers were designed using LAMP designer (Premier Biosoft) or an in-house design algorithm. For added specificity, molecular beacons or probes targeting the amplified products were designed manually or using Beacon designer (Premier Biosoft). Designed primer sets and beacons were further analyzed for specificity using BLAST against the NCBI nucleotide database, including human transcriptome, influenza virus, and non-human coronavirus. Various primer sets and probes were designed and screened for reaction speed.

The inventive primer sets are summarized in Table 3, which include, at a minimum, a forward inner primer (FIP) and backward inner primer (BIP). Additionally, the primer sets typically also include at least two additional primers selected from the forward outer primer (F3), backward outer primer (B3), forward loop primer (LF) and backward loop primer (LB).

TABLE 3

| LAMP Primer Sets | | | | | | |
| --- | --- | --- | --- | --- | --- | --- |
| Set | F3 | B3 | FIP | BIP | LF | LB |
| Set-1 | SEQ ID No: 1 | SEQ ID No: 2 | SEQ ID No: 3 | SEQ ID No: 4 | SEQ ID No: 5 | SEQ ID No: 6 |
| Set-2 | SEQ ID No: 7 | SEQ ID No: 8 | SEQ ID No: 9 | SEQ ID No: 10 | SEQ ID No: 11 | SEQ ID No: 12 |
| Set-3 | SEQ ID No: 13 | SEQ ID No: 14 | SEQ ID No: 15 | SEQ ID No: 16 | SEQ ID No: 17 | SEQ ID No: 18 |
| Set-4 | SEQ ID No: 19 | SEQ ID No: 20 | SEQ ID No: 21 | SEQ ID No: 22 | SEQ ID No: 23 | SEQ ID No: 24 |
| Set-5 | SEQ ID No: 25 | SEQ ID No: 26 | SEQ ID No: 27 | SEQ ID No: 28 | SEQ ID No: 29 | SEQ ID No: 30 |
| Set-6 | SEQ ID No: 31 | SEQ ID No: 32 | SEQ ID No: 33 | SEQ ID No: 34 | SEQ ID No: 35 | SEQ ID No: 36 |
| Set-7 | SEQ ID No: 37 | SEQ ID No: 38 | SEQ ID No: 39 | SEQ ID No: 40 | SEQ ID No: 41 | SEQ ID No: 42 |
| Set-8 | SEQ ID No: 43 | SEQ ID No: 44 | SEQ ID No: 45 | SEQ ID No: 46 | SEQ ID No: 47 | SEQ ID No: 48 |
| Set-9 | SEQ ID No: 49 | SEQ ID No: 50 | SEQ ID No: 51 | SEQ ID No: 52 | SEQ ID No: 53 | SEQ ID No: 54 |
| Set-10 | SEQ ID No: 57 | SEQ ID No: 58 | SEQ ID No: 59 | SEQ ID No: 60 | SEQ ID No: 61 | SEQ ID No: 62 |
| Set-11 | SEQ ID No: 63 | SEQ ID No: 64 | SEQ ID No: 65 | SEQ ID No: 66 | SEQ ID No: 67 | SEQ ID No: 68 |
| Set-12 | SEQ ID No: 69 | SEQ ID No: 70 | SEQ ID No: 71 | SEQ ID No: 72 | SEQ ID No: 73 | SEQ ID No: 74 |
| Set-13 | SEQ ID No: 63 | SEQ ID No: 86 | SEQ ID No: 65 | SEQ ID No: 87 | SEQ ID No: 67 | SEQ ID No: 88 |
| Set-14 | SEQ ID No: 89 | SEQ ID No: 90 | SEQ ID No: 91 | SEQ ID No: 92 | SEQ ID No: 93 | SEQ ID No: 94 |
| Set-15 | SEQ ID No: 89 | SEQ ID No: 96 | SEQ ID No: 97 | SEQ ID No: 98 | SEQ ID No: 99 | SEQ ID No: 94 |
| Set-16 | SEQ ID No: 100 | SEQ ID No: 101 | SEQ ID No: 102 | SEQ ID No: 103 | SEQ ID No: 99 | SEQ ID No: 94 |
| Set-17 | SEQ ID No: 89 | SEQ ID No: 96 | SEQ ID No: 91 | SEQ ID No: 92 | SEQ ID No: 93 | SEQ ID No: 94 |

Typically, 3 to 5 µL of RNA standards or genomic RNA or genomic RNA extracted from negative nasal swab matrix or negative controls (NTC=nuclease free water or Tris buffer, no template control) served as template for RTLAMP reactions. 10-25 µl total volume reactions were prepared on ice as mixes containing formulations including 1× amplification buffer comprising 10-40 mM Tris-HCl, 0-0.5% Tween 20, 0-300 mM Trehalose, 5-70 mM KCl, 4-41 mM MgSO$_4$, 10-20 mM (NH$_4$)$_2$SO$_4$, 0-2 mM TCEP and 1.6-2 mM each dCTP, dGTP, dATP and dTTP. NEB Bst2 polymerase (NEB CN #M0537L) and RTx Warmstart reverse transcriptase (NEB CN #M0380S) enzymes. Primers (2 µM inner primers, 0.2 µM outer primers, and 0.8 µM Loop primers) were added to individual reactions or directly to master mixes as required per experimental design. Molecular beacons (0.2 µM) or 200 nM To-Pro dye was also added to the master mix, as indicated in the examples below. Amplification reactions were prepared with the standard 6-primer composition. Master mixes were distributed to individual sample templates, vortexed and centrifuged briefly and each reaction loaded into individual wells of a 96 or 384 well plate (Roche CN #4729692001 or BioRad CNhs19605). Reactions were carried out at temperatures ranging from 60–67° C. and fluorescence monitored on either a Roche LightCycler 96 Real-Time PCR instrument or a BioRad CFX96 real time cycler. Target amplification was monitored via intercalating dye or molecular beacon probe binding to target resulting in release of molecular beacon fluorescence intramolecular quenching.

Example 2: Amplification Reaction Kinetics

Input samples were RNA molecular standards generated from in vitro transcription of 900-1500 bp gene fragments, including those of SARS-CoV-2 and common human coronavirus.

An RNA molecular standard or genomic RNA was diluted to various concentrations ranging from 50-5000 copies/reaction to assess the sensitivity of the indicated primer set (Table 3). Standards were serially diluted with 0.1 mg/mL Poly A carrier RNA in PBS (Sigma) and used as template for amplification in RTLAMP reactions. ToPro™ or Syto™ dye or a compatible wavelength version within the same dye set family (Life Technologies; green or red fluorescent carbocyanine nucleic acid stain) was used for the detection of the amplified product. The master mix was prepared as described in Example 1.

This example shows that using this set of primers and the loop mediated amplification method, fast amplification kinetics are achieved. Results are summarized in Table 4, in which the Time to Positive ($T_p$) was calculated by using an in-house developed algorithm. NT indicates concentrations not tested. Results are classified by the time to positive (NT means "not tested" and "no call" indicates that no amplification was detected).

TABLE 4

Time to Positive Dye Detection

| Primer Set | Time to Positive (minutes) | | | |
|---|---|---|---|---|
| | 5,000/reaction | 500/reaction | 50/reaction | NTC |
| Set-1 | 7.8 | 9.1 | 13.0 | 37.2 |
| Set-2 | 5.8 | 6.6 | 8.4 | no call |
| Set-3 | NT | 8.2 | 9.2 | no call |
| Set-4 | 8.6 | 9.7 | 13.3 | no call |

TABLE 4-continued

Time to Positive Dye Detection

| Primer Set | Time to Positive (minutes) | | | |
|---|---|---|---|---|
| | 5,000/reaction | 500/reaction | 50/reaction | NTC |
| Set-5 | 8.54 | 10.0 | no call | no call |
| Set-6 | 6.8 | 8.0 | no call | no call |
| Set-7 | 7.7 | 8.8 | 12.4 | no call |
| Set-8 | 6.7 | 8.3 | 10.5 | 24.0 |
| Set-9 | 6.5 | 7.8 | 9.6 | no call |
| Set-10 | 5.6 | 6.5 | 9.6 | 28.3 |
| Set-11 | 4.8 | 5.3 | 6.5 | no call |
| Set-12 | 7.7 | 9.0 | 11.9 | no call |
| Set-14 | 8.5 | 9.7 | 11 | no call |

A negative nasal swab matrix was spiked with genomic material from common human coronaviruses strain 229E, NL63, and OC43. The corresponding extracted nucleic acids or DNAs were used as templates in RT-LAMP reactions containing the LAMP primers and compared to 500-5000 copies/reaction of SARS-COV-2 RNA standard for specificity.

TABLE 5

Cross-Reactivity Dye Detection

| Primers | 5000 | 500 | 229E | NL63 | OC43 |
|---|---|---|---|---|---|
| Set-1 | 7 | 8.5 | no call | no call | no call |
| Set-4 | 7 | 7.9 | no call | no call | no call |
| Set-8 | 6.3 | 7.2 | no call | no call | no call |
| Set-11 | 4.8 | 5.3 | no call | no call | no call |

Example 3: Molecular Beacon Detection

To provide an additional level of direct sequence based detection of amplified product (as opposed to indirect dye detection), molecular beacons (MB1-MB14; see Table 2) targeting unique nucleotides within the SARS-CoV-2 amplicon of primer sets with promising times-to-positive combined with sensitivity, were designed and utilized for detection of amplification from RNA standards (Table 4). The molecular beacon probe was designed with 5' fluorophore/3' quencher modifications (6-Carboxyfluorescein (FAM)) and Black Hole Quencher 1 (BHQ1) and Locked Nucleic Acid (+) included to provide target-specific fluorescent detection.

10-25 µL total volume reactions were evaluated utilizing 25 to 500 copies/reaction of SARS-CoV-2 RNA standard or genomic RNA as template input according to the methods described in Examples 1 and 2. While use of a Molecular Beacon for detection resulted in a slight increase in reaction Tp, the ability to directly detect amplification products based on sequence, and thereby distinguish closely related species, provides a reasonable tradeoff.

TABLE 6

Time to Positive Probe Detection

| Primers | Beacon | Time to Positive (minutes) | | |
|---|---|---|---|---|
| | | 500 | 50 | 25 | NTC |
| Set-1 | MB1 | 10.1 | 14.7 | 13.9 | no call |
| Set-8 | MB2 | 9.1 | 12.0 | 12.4 | no call |
| Set-9 | MB4 | 9.4 | 14.9 | 14.5 | no call |
| Set-9 | MB8 | 8.1 | 12.7 | NT | no call |

TABLE 6-continued

Time to Positive Probe Detection

| | | Time to Positive (minutes) | | | |
|---|---|---|---|---|---|
| Primers | Beacon | 500 | 50 | 25 | NTC |
| Set-9 | MB9 | 8.2 | 10.6 | NT | no call |
| Set-9 | MB10 | 9.2 | 11.6 | NT | no call |
| Set-11 | MB5 | 7.1 | 8.3 | 8.9 | no call |
| Set-11 | MB7 | NT | 7.8 | 8.5 | no call |
| Set-12 | MB6 | 11.3 | 13.7 | 14.7 | no call |
| Set-9 | MB11 | 7.1 | 8.5 | 12.6 | no call |
| Set-14 | MB14 | NT | 13.7 | 13.7 | no call |

Selected primer set and Molecular Beacon pair was additionally tested for specificity by comparing reactions with 500 to 5000 copies/reaction of SARS-CoV-2 RNA standard to reactions with approximately $5 \times 10^5$ copies/reaction of RNA standards or extracted nucleic acids from negative nasal swab matrix spiked with closely related common human coronavirus strain 229E, NL63, OC43, or SARS-related coronavirus. When the amplification reactions were performed as described in Example 1 and 2, the primer and Molecular Beacon pair tested had no cross-reactivity against common human coronavirus (Table 7).

TABLE 7

Cross Reactivity Probe Detection

| Primers | Beacon | 5000 | 500 | 229E | NL63 | OC43 | SARS |
|---|---|---|---|---|---|---|---|
| Set-8 | MB2 | 8.4 | 9.1 | no call | no call | no call | NT |
| Set-10 | MB3 | 6.3 | 7.1 | NT | NT | NT | no call |
| Set-12 | MB6 | 10.1 | 11.3 | NT | NT | NT | no call |

Example 4: Multi-Target Amplification

The genomic sequence of SARS-CoV-2, like all viruses, is subject to mutation and natural selection. Given the potential lethality and relatively high transmissibility of SARS-CoV-2, it would be beneficial for an assay to detect the presence of more than one genomic target. Thus, if one portion of the virus has mutated, the virus can still be detected via a second location. This can be achieved by performing two separate amplification assays. However, time, personnel and resources are limited. Accordingly, it is advantageous if two or more genomic targets can be assessed simultaneously in the same reaction well. This is commonly performed with standard PCR assays, which typically utilize two primers per amplification locus. LAMP, however, typically includes six primers comprising eight separate hybridization sites. This creates significantly higher potential for primer:primer interactions that could interfere with targeted amplification or lead to off-target amplification that could be confused for on-target amplification (leading to a mistaken positive diagnosis for COVID-19). Set-9 and Set-11 were confirmed in silico to present little potential for off-target amplification from primer-primer interactions.

First, Set-9 and Set-11 were combined to amplify an RNA molecular standard, diluted to 25, 50, or 500 copies per reaction various concentrations ranging from 5-500 copies/reaction to assess the sensitivity combined primer set. Standards were serially diluted with 0.1 mg/mL Poly A carrier RNA in PBS (Sigma) and used as template for amplification in RTLAMP reactions. ToPro™ or Syto™ dye was used for the detection of the amplified product. The master mix was prepared as described in Example 1. Amplification was detected at 5.3 minutes (time to positive) for 500 copies/reaction; 6.2 minutes for 50 copies/reaction and 6.5 minutes for 25 copies/reaction. No amplification was detection with the negative control, as expected.

A negative nasal swab matrix was spiked with genomic material from common human coronaviruses strain 229E, NL63, and OC43. The corresponding extracted nucleic acids or DNAs were used as templates in RT-LAMP reactions containing combined LAMP primer set and compared to 50-5000 copies/reaction of SARS-COV-2 RNA standard or extracted genomic RNA from negative nasal swab matrix for specificity. No amplification was detected for any potentially cross-reacting species.

To provide an additional level of direct sequence-based detection of amplified product (as opposed to indirect dye detection), molecular beacons (MB5 and MB11; See Table 2) targeting unique nucleotides within the SARS-CoV-2 ORF1b and N gene amplicons, respectively, were included to provide target-specific fluorescent detection. 10-25 µL total volume reactions were evaluated utilizing 25, 50 or 500 copies/reaction of SARS-CoV-2 RNA standard as template input according to the methods described in Examples 1 and 2. The combined primer set (Set-9 and Set-11) plus two beacons (MB5 and MB11) detected application at 6.5 minutes (time to positive) at 500 copies/reaction; at 7.7 minutes at 50 copies/reaction and at 7.8 minutes at 25 copies/reaction. No amplification was detected with a no template (negative) control.

The combined primer set and Molecular Beacon pair was additionally tested for specificity by comparing reactions with 50 to 5000 copies/reaction of SARS-CoV-2 RNA standard or extracted genomic RNA from negative nasal swab matrix to reactions with approximately $5 \times 10^5$ copies/reaction of RNA standards or extracted nucleic acids from negative nasal swab matrix spiked with closely related common human coronavirus strain 229E, NL63, OC43, or SARS-related coronavirus. When the amplification reactions were performed as described in Example 1 and 2, the primer (Set-9 and Set-11, together) and Molecular Beacon pair (MB5 and MB 11, together) detected no cross-reactivity against common human coronavirus 229E, human coronavirus NL83, human coronavirus OC43, and SARS-CoV (2003).

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A composition comprising a set of polynucleotides comprising:
a primer set comprising a forward outer primer comprising SEQ ID NO: 63, a backward outer primer comprising SEQ ID NO: 86, a forward inner primer comprising SEQ ID NO: 65, a backward inner primer comprising SEQ ID NO: 87, a forward loop primer comprising SEQ ID NO: 67, and a backward loop primer comprising SEQ ID NO: 88.

2. The composition of claim 1, further comprising a probe.

3. The composition of claim 2, wherein the probe comprises a label.

4. The composition of claim 3, wherein the probe is a labeled polynucleotide.

5. The composition of claim 4, wherein the labeled polynucleotide comprises a sequence selected from the group consisting of nucleotides 5-29 of SEQ ID NO.: 77 and nucleotides 5-29 of SEQ ID NO.: 79.

6. The composition of claim 5, wherein the labeled polynucleotide comprises SEQ ID NO.: 77 or SEQ ID NO.: 79.

7. The composition of claim 5, wherein the sequence of the labeled polynucleotides is SEQ ID NO.: 77.

8. The composition of claim 2, wherein the probe is a molecular beacon comprising a fluorophore, a quencher, and a polynucleotide.

9. The composition of claim 8, wherein the molecular beacon comprises a sequence selected from the group consisting of nucleotides 5-29 of SEQ ID NO.: 77 and nucleotides 5-29 of SEQ ID NO.: 79.

10. The composition of claim 9, wherein the molecular beacon comprises a sequence selected from the group consisting of SEQ ID NO.: 77 and SEQ ID NO.: 79.

11. A kit comprising a composition according to claim 1.

12. The kit of claim 11, further comprising a strand displacement polymerase and reverse transcriptase.

13. The kit of claim 12, further comprising a molecular beacon comprising a fluorophore, a quencher, and a polynucleotide, wherein the polynucleotide comprises a sequence selected from the group consisting of nucleotides 5-29 of SEQ ID NO.: 77 and nucleotides 5-29 of SEQ ID NO.: 79.

14. The kit of claim 13, wherein the polynucleotide of the molecular beacon consists of a sequence selected from the group consisting of SEQ ID NO.: 77 and SEQ ID NO.: 79.

15. A method of detecting SARS-CoV-2 in a test sample, the method comprising:
(a) extracting nucleic acid from the test sample;
(b) amplifying a target sequence by reacting the nucleic acid extracted in step (a) with a reaction mixture comprising a strand displacement DNA polymerase and reverse transcriptase and a sequence-specific primer set, wherein said sequence-specific primer set is Set-13, wherein Set-13 comprises a forward outer primer comprising SEQ ID NO: 63, a backward outer primer comprising SEQ ID NO: 86, a forward inner primer comprising SEQ ID NO: 65, a backward inner primer comprising SEQ ID NO: 87, a forward loop primer comprising SEQ ID NO: 67, and a backward loop primer comprising SEQ ID NO: 88; and
(c) detecting the presence or absence of an amplified product of step (b); wherein the presence of said amplification product is indicative of the presence of SARS-CoV-2 in the test sample.

16. The method of claim 15, wherein the amplification in step (b) of the target sequence is performed between about 60° C. and about 67° C. for less than 30 minutes.

17. The method of claim 16, wherein the amplification step is performed for less than fifteen minutes.

18. The method of claim 17, wherein the amplification step is performed for less than twelve minutes.

19. The method of claim 18, wherein the amplification step is performed for less than nine minutes.

20. The method of claim 15, wherein detecting the presence or absence of the amplification product comprises hybridizing the amplified product with a probe comprising a polynucleotide attached to a label.

21. The method of claim 20, wherein the label is a fluorophore.

22. The method of claim 21, wherein the fluorophore is covalently attached to a terminus of the polynucleotide.

23. The method of claim 20, wherein the labeled polynucleotide comprises a sequence selected from the group consisting of nucleotides 5-29 of SEQ ID NO.: 77 and nucleotides 5-29 of SEQ ID NO.: 79.

24. The method of claim 23, wherein the sequence of the labeled polynucleotide comprises SEQ ID NO.: 77 or SEQ ID NO.: 79.

* * * * *

SEQUENCE LISTING

```
<160> NUMBER OF SEQ ID NOS: 103

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggaccaggaa ctaatcagac a                                                 21

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctgcggtaa ggcttgag                                                     18

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
accacgttcc cgaaggtgtc agcgttcttc ggaatgtc                               38

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgacctacac aggtgccatc aaggctctgt tggtgggaat                             40

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
```
gacttccatg ccaatgcg                                                 18

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctgaataag catattgacg catac                                         25

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
accccaaaat cagcgaaa                                                 18

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
attggaacgc cttgtcc                                                  17

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atcgcgcccc actgccaccc cgcattacgt tt                                 32

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgtcggcccc aaggtttatc cttgccatgt tgagtg                             36

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cagttgaatc tgagggtcca                                               20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtcttggttc accgctct                                                 18

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aaaaggcttc tacgcagaa                                                19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctttaccag acattttgct c                                             21

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
actgctgcct ggagttgaat cagtcaagcc tcttctcg                           38

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctgctagaat ggctggcaat gtggttcaat ctgtcaagca                         40

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
actgttgcga ctacgtgat                                                19

```
<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcggtgatgc tgctct                                                       16

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aggaactgat tacaaacatt gg                                                22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttttgtatgc gtcaatatgc tt                                                22

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaggtgtgac ttccatgcca acaatttgcc cccagc                                 36

<210> SEQ ID NO 22
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gggaacgtgg ttgacctaca gacttgatct ttgaaatttg gatc                        44

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgcgcgacat tccgaa                                                       16
```

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggtgccatca aattggatga                                                   20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcaaagatca agtcattttg ct                                                22

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcctgagttg agtcagc                                                      17

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtctctgcgg taaggcttga atacaaaaca ttcccaccaa c                            41

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcaaactgtg actcttcttc ctgtgctcat ggattgttgc a                            41

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atcagccttc ttcttttgt cc                                                 22

```
<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgcagatttg gatgatttct cc                                              22

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cagaaatcaa tactgagtcc tct                                             23

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtagccaaat cagatgtgaa c                                               21

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cacagaattt tgagcagttt caagagttca gaggctgctc gtg                       43

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgtgttttac agaaggccgc catagcatca atgagtctca gt                        42

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcgggagaaa attgatcgta c                                               21

<210> SEQ ID NO 36
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ataacaatac tagatggaat ttcacagt                                      28

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
caaattgttg aatcctgtgg t                                             21

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aaattccatc tagtattgtt atagcg                                        26

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aatgcataaa gaggactcag tattgatttc aattttaaag ttacaaaagg aaaagct      57

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cagaggctgc tcgtgttgtc acgcacagaa ttttgagc                           38

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgttcaccaa tattccaggc a                                             21

<210> SEQ ID NO 42
<211> LENGTH: 20
```

<212> TYPE: DNA
<213> ORGANISM: Artificial Sequence
<220> FEATURE:
<223> OTHER INFORMATION: Description of Artificial Sequence: Synthetic primer

<400> SEQUENCE: 42
cgatcaattt tctcccgcac					20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
gtcaagcctc ttctcgttc					19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
cttagtgaca gtttggcctt					20

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
ccgccattgc cagccaaaca gttcaagaaa ttcaactcc					39

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
gatgctgctc ttgctttgct ggcctttacc agacattttg c					41

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gagaagttcc cctactgctg					20

<210> SEQ ID NO 48
<211> LENGTH: 21
<212> TYPE: DNA

<213> ORGANISM: Artificial Sequence
<220> FEATURE:
<223> OTHER INFORMATION: Description of Artificial Sequence: Synthetic primer

<400> SEQUENCE: 48
tgacagattg aaccagcttg a    21

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
aatttcaaag atcaagtcat tttgc    25

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
gttgagtcag cactgctc    18

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
aaggcttgag tttcatcagc ctcgcataca aaacattccc ac    42

<210> SEQ ID NO 52
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
gcagagacag aagaaacagc aaacattgtt gcaattgttt ggagaa    46

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 53 tcttttgtc cttttaggc tctg    24

<210> SEQ ID NO 54
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 54
ctcttcttcc tgctgcagat ttgg                                           24

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
cacgccaaat ttcaaagatc aagtcatggc gtg                                 33

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
cagctgcttg acagattgaa ccagcagctg                                     30

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
caaattgttg aatcctgtgg t                                              21

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aaattccatc tagtattgtt atagcg                                         26

<210> SEQ ID NO 59
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
aatgcataaa gaggactcag tattgatttc aattttaaag ttacaaaagg aaaagct       57

<210> SEQ ID NO 60
<211> LENGTH: 38
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 60
cagaggctgc tcgtgttgtc acgcacagaa ttttgagc                                   38

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgttcaccaa tattccaggc a                                                     21

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgatcaattt tctcccgcac                                                       20

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tcttatcaga ggcacgtca                                                        19

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tgtctcacca ctacgacc                                                         18

<210> SEQ ID NO 65
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
acgtttgatg aacacatagg gcttaaagat ggcacttgtg gc                              42

<210> SEQ ID NO 66
<211> LENGTH: 37
<212> TYPE: DNA
<213> ORGANISM: Artificial Sequence
<220> FEATURE:
<223> OTHER INFORMATION: Description of Artificial Sequence: Synthetic
```

```
        primer

<400> SEQUENCE: 66
tcggatgctc gaactgcact gccttcgagt tctgcta                              37

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ttcaagttga ggcaaaacgc                                                 20

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
catggtcatg ttatggttga gc                                              22

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
atgtccaaat tttgtatttc cctt                                            24

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gctttaacaa aatcgcccg                                                  19

<210> SEQ ID NO 71
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gcaactggat agacagatcg aattctatcc ataatcaaga ctattcaacc a              51

<210> SEQ ID NO 72
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 72
caccaaatga atgcaaccaa atgtgtctgc catgaagttt cacc                       44

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
catcaagctt tttcttttca accc                                             24

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cctttcaact ctcatgaagt gtg                                              23

<210> SEQ ID NO 75
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
cacggtgact cttcttcctg ctcaccgtg                                        29

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
cgagtcctgc tgcagatttg gactcg                                           26

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
cagctcatgg tcatgttatg gttgagctg                                        29

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 78
cacactttca actctcatga agtgtg                                      26

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
cagctcatgg tcatgttatg gttgagctg                                   29

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
cgagtcctgc tgcagatttg gactcg                                      26

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
catgtcctgc tgcagatttg gacatg                                      26

<210> SEQ ID NO 82
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
cacttcctgc tgcagatttg gaagtg                                      26

<210> SEQ ID NO 83
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
cacgcgtgac tcttcttcct gctgcagacg cgtg                             34

<210> SEQ ID NO 84
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
```
cacgcttctt cctgctgcag atttgaagcg tg                                    32

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
cagactcttc ttcctgctgc agagtctg                                         28

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gagggacaag gacaccaag                                                   19

<210> SEQ ID NO 87
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tcggatgctc gaactgcact gtctcaccac tacgacc                               37

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ggtagcagaa ctcgaaggca t                                                21

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aagagacagg tacgttaata gt                                               22

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ttagaccaga agatcaggaa c                                              21

<210> SEQ ID NO 91
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
aagcgcagta aggatggcta tagcgtactt cttttcttg c                         41

<210> SEQ ID NO 92
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tgcgtactgc tgcaatattg ttttaacacg agagtaaacg taaa                     44

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tgtaactagc aagaatacca cg                                             22

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cgtgagtctt gtaaaacctt ct                                             22

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
cacgtgagtc ttgtaaaacc ttctcacgtg                                     30

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gaagatcagg aactctagaa ga                                             22

<210> SEQ ID NO 97
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
acacaatcga agcgcagtaa gttttcttgc tttcgtggta t                          41

<210> SEQ ID NO 98
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gcgtactgct gcaatattgt tttaacacga gagtaaacgt aaa                        43

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tggctagtgt aactagcaag a                                                21

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
acgttaatag ttaatagcgt actt                                             24

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tcaggaactc tagaagaatt ca                                               22

<210> SEQ ID NO 102
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
acaatcgaag cgcagtaagg ttttcttgct tcgtggtat                             40

```
<210> SEQ ID NO 103
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
tgcgtactgc tgcaatattg tttttaacac gagagtaaac gtaaa                45
```